United States Patent
Tkachuk

(10) Patent No.: US 6,737,271 B1
(45) Date of Patent: May 18, 2004

(54) COMPOUND, COMPOSITION AND METHOD FOR THE TREATMENT OF INFLAMMATORY AND INFLAMMATORY-RELATED DISORDERS

(75) Inventor: Zenoviy Tkachuk, Washington, DC (US)

(73) Assignee: Biocell Laboratories, Washington, DC (US)

( * ) Notice: Subject to any disclaimer, the term of this patent is extended or adjusted under 35 U.S.C. 154(b) by 0 days.

(21) Appl. No.: 09/534,509

(22) Filed: Mar. 24, 2000

(51) Int. Cl.$^7$ .......................... C12N 5/00; A01N 63/00; A01N 43/04; C07H 21/02; C07H 21/04

(52) U.S. Cl. .................. 435/375; 424/93.2; 424/93.21; 536/23.1; 536/23.74; 514/44

(58) Field of Search ............................. 424/93.2, 93.21; 536/23.1, 23.74, 23.2; 435/375; 514/44

(56) References Cited

U.S. PATENT DOCUMENTS

| | | | |
|---|---|---|---|
| 3,615,654 A | * 10/1971 | Ayukawa et al. | 99/9 |
| 3,914,450 A | * 10/1975 | Robbins et al. | 426/533 |
| 5,712,256 A | 1/1998 | Kulkarni et al. | 514/44 |

FOREIGN PATENT DOCUMENTS

WO        94-02595    *   2/1994

OTHER PUBLICATIONS

Gallin et al., Inflammation: Basic Principles and Clinical Correlates, 1992, Second Edition, Raven Press, New York, p. 1–4.*
Iyer et al., Absolute mRNA levels and transcriptional initiation rates in Saccharomyces cerevisiae, May 1996, Proc. Natl. Acad. Sci., vol. 93, pp. 5208–5212.*
Tait et al., A Phase I Trail of Retrovrial BRCA1sv Gene Therapy in Ovarian Cancer, Nov. 1997, Clinical Cancer Research, pp. 1959–1968.*
Prokopenko, L.H., Siplivaya, L.E., Erythrocytes as modulators of immunologic reactions, Uspekhi Phiziologicheskikh Nauk., V.23, N.4, P. 89–106, 1992.
Karalnik, B.V., Erythrocytes, their receptors, and immunity, Uspekhi Sovremennoy Biologii., V.112, N.1, p. 52–61, 1992.
Kordyum, V.A., Kirilova, V.S., Likhachova, L.I., Biological action of exogenous nucleic acids, Visnyk ASC USSR, V.41, N.6, p. 67–78, 1977.
Courtright, L.J., Kuzell, W.C., Sparing effect of neurological deficit and trauma on the course of adjuvant arthritis in the rat, Ann. rheum, dis., N.24, p. 360–367, 1965.
Terskov, A., Gitelzon, I., The method of chemical (acid) erythrograms, Biophisika V.1, N.20, 1956.
Kosaka, H., Harada, N., Watanbe, M., Yoshihara, H., Katsuki, Y., Shiga, T., Synergistic stimulation of nitric oxide 1 and tumor necrosis factor, Biochemical and Biophysical Research Communications, V.189, N.1, p. 392–397, 1992.
Huot, A.E., Kruszyna, H., Smith, R.P., Hacker, M.P., Formation of nitric oxide hemoglobin in erythrocytes co–cultured with alveolar macrophages taken from bleomycin treated rats, Biochemical and Biophysical Research Communications, V.182, N.1, p. 151–157, 1992.
Sato, Y., Kamo, S., Takahashi, T., Suzuki, Y., Mechanism of free radical–induced hemolysis of human erythrocytes: hemolysis by water–soluble radical initiator, Biochemistry, N.34, p. 8940–8949, 1995.
Eich, R.F., Li, T., Lemon, D.D., Doherty, D.H., Curry, S.R., Aitken, J.F., Matthews, A.J., Johnson, K.A., Smith, R.D., Phillips, G.N., Olsen, J.S., Mechanism of NO–induced oxidation of myoglobin and hemoglobin, Biochemistry, N.35, p. 6976–6983, 1996.
Mueller, B., Maass, B., Krause, W., Witt, W., Limitation of myocardial unoerfused area and necrotic zone 24 hours and 7 days after coronary artery ligation in rats by the stable prostacyclin analogue iloprost, Prostaglandins Leukotrienes and Medicine, N.21, p. 331–340, 1986.
Khawaja, J., Interaction of ribosomes and ribosomal subparticles with endoplasmic reticulum membranes in vitro: Effect of spermine and magnesium, Biochimica et Biophisic Acta, N.254, p. 117–128, 1971.
Cundliffe, E., Intracellular distribution of ribosomes and polyribosomes in *bacillus megaterium*, Mol. Biol., N.52, p. 467–481, 1970.
Hibbs, J.B., Taintor, R.R., Vavrin, Z., Rachlin, E.M., Nitric oxide: A cytotoxic activated macrophage effector molecule, Biochemical and Biophysical Research Communications, V.157, N.1, p. 87–94, 1988.
Scott–Burden, T., Hawtrey, A.O., Preparation of ribosome–free membranes from rat liver microsomes by means of lithium chloride, Biochem,J., N.115, p. 1063–1069, 1969.
Mainwaring, W.I.P., The effect of age on protein synthesis in mouse liver, Biochem.J., N.113, p. 869–878, 1969.

(List continued on next page.)

*Primary Examiner*—Shin-Lin Chen
(74) *Attorney, Agent, or Firm*—Westerman, Hattori, Daniels & Adrian LLP

(57) ABSTRACT

The present invention concerns a compound consisting of RNA, in particular RNA extracted from yeast, a pharmaceutical composition comprising such RNA and a method for the treatment of inflammatory and inflammatory-related disorders comprising administering to a patient in need of such torment a pharmaceutical composition comprising an amount effective to ameliorate the symptoms of inflammation or inflammatory-related disorder of ribonucleic acid and a pharmaceutically acceptable vehicle, carrier, or diluent. The exogenous yeast RNA used in the present invention has a pronounced membrane-stabilizing action in a wide range of concentrations. At the same time, yeast RNA normalizes metabolism of arachidonic acid and levels of its key metabolites, thromboxane and leukotriene. Its anti-inflammatory action is accompanied by normalization of the activity of NO-synthetase and anti-oxidant activity.

24 Claims, No Drawings

OTHER PUBLICATIONS

Yan, L., Vandivier, W., Suffredini, A.F., Danner, R.L., Human polymorphonuclear leukocytes lack detectable nitric oxide synthase activity, The Journal of Immunology, p. 1825–1834, 1994.

Arnet, U.A., McMillan, A., Dinnerman, J.L., Ballerman, B., Lowenstein, C., Regulation of endothelial nitric–oxide synthase during hypoxia, Journal of Biological chemistry, V.271, N.25, p. 15069–15073, 1996.

Balligand, J.L., Kobzik, L., Han, X., Kaye, D.M., Belhassen, L. O'Hara, D.S., Kelly, R.A., Smith, T.W., Michel, T., Nitric oxide–dependent parasympathetic signaling is due to activation of constitutive endothelial (type III) nitric oxide synthase in cardiac myocytes, The Journal of Biological Chemistry, V.270, No.24, p. 14582–14586, 1995.

Salkowski, C.A., Detore, G., McNally, R., Rooijen, N.v., Vogel, S.N., Regulation of inducible nitric oxide synthase messenger RNA expression and nitric oxide production by lipopolysaccaride in vivo, The Journal of Immunology, p. 905–912, 1996.

Peng, HB., Spiecker, M., Liao, J.K., Inducible nitric oxide: An autoregulatory feedback inhibitor of vascular inflammation, The Journal og Immunology, p. 1970–1976, 1998.

Gumina, R.J., Schultz, J.E., Yao, Z., Kenny, D., Warltier, D.C., Newman, P.J., Gross, G.J., Antibody to platelet/endothelial cell adhesion molecule–1 reduces myocardial infact size on a rat model of ischemia–reperfusion injury, Circulation, V.94, N.12, p. 3327–3333, 1996.

Levine, L., Morgan, R.A., Lewis, R.A., Austen K.F., Clark, D.A., Marfat, A., Corey, E.J., Radioimmunoassay of the leukotrienes of slow reacting substance of anaphylaxis, Proc. Natl. Acad. Sci. USA, V.78, N.12, p. 7692–7696, 1981.

Rodionova, N.P., Shapot, V.S., Ribonucleic acids of the endoplasmic reticulum of animal cells, Biochim. Biophys. Acta., N.129, p. 206–209, 1966.

Lukacs, G.L., Kapus, A., Nanda, A., Romanek, R., Grinstein, S. Proton conductance of the plasma membrane: properties, regulation and functional role, American Physiological Society, p. C3–C14, 1993.

Moscat, J., Moreno, F., Herrero, C., Iglesias, S., Garcia–Barreno, P., Arachidonic acid releasing systems in pig aorta endothelial cells, Biochemical and Biophysical Research Communications, V.139, N.3, p. 1098–1103, 1986.

Zavodnik, I.B., PiletSkaya, T.P., Acid–induced Haemolysis of Human Erythrocytes, Belarussian Acad. Sci., p. 1106–1112, 1997.

Anderson, J.L., Carlquist, J.F., Muhlestein, J.B., Horne, B.D., Elmer, S.P., Evaluation of C–reactive protein, an inflammatory marker, and infectious serology as risk factors for coronary artery disease and myocardial infarction, J Am Coll Cardiol, V.32, N.1, p. 35–41, 1998 (abstract).

Arnet, U.A., McMillan, A., Dinerman, J.L., Ballermann, B., Lowenstein, C.J., Regulation of endothelial nitric–oxide synthase during hypoxia, J Biol Chem, V.271, N.25, p. 15069–15073, 1996 (abstract).

Arvinte, T., Cudd, A., Schultz, B., Nicolau, C., Low–pH association of proteins with the membranes of intact red blood cells. II. Studies of the mechanism, Biochem Biophys Acta, V.981, N.1, p. 61–8, 1989 (abstract).

Balligand, J.L., Kobzik, L., Han, X., Kaye, D.M., Belhassen, L., O'Hara, D.S., Kelly, R.A., Smith, T.W., Michel, T., Nitric oxide dependent parasympathetic signaling is due to activation of constitutive endothelial (type III) nitric oxide synthase in cardiac myocytes, J Biol Chem, V.270, N.24, p.14582–14586, 1995 (abstract).

Balezina, T.I., Fadeeva, L.L., Zemskov, V.M., Korneeva, I.E., Loidina, G.I., Interferonogenic and antiviral activity of the tobacco mosaic virus, tilorone and sodium nucleinate, Antibiotiki, V.21, N3, p. 250–254, 1976 (abstract).

Bashford, C.L., Alder, G.M., Menestrina, G., Micklem, K.J., Murphy, J.J., Pasternak, C.A., Membrane damage by hemolytic viruses, toxins, complement, and other cytotoxic agents. A Common mechanism blocked by divalent cations, J Biol Chem, V.261, N.20, p. 9300–9308, 1986 (abstract).

Bradley, P.P., Priebat, D.A., Christensen, R.D., Rothstein, G., Measurement of cutaneous inflammation: estimation of neutrophil content with an enzyme marker, J Invest Dermatol, V.78, N.3, p. 206–209, 1982 (abstract).

Calver, A., Collier, J., Vallance, P., Inhibition and stimulation of nitric oxide synthesis in the human forearm arterial bed of patients with insulin–dependent diabetes, J Clin Invest, V.90, N.6, p. 2548–2554, 1992 (abstract).

Calver, A., Collier, J., Moncada, S., Vallance, P., Effect of local intra–arterial NG–monomethyl–L–arginine in patients with hypertension: the nitric oxide dilator mechanism appears abnormal, J Hypertens, V.10, N.9, P.1025–1031, 1992 (abstract).

Chen, L.Y., Mehta, J.L., Evidence for the presence of L–arginine–nitric oxide pathway in human red blood cells on platelet function, J Cardiovasc Pharmacol, V.32, N.1, P57–61, 1998 (abstract).

Cooper, K.D., Shukla, J.B., Rennert, O.M., Polyamine comparmentalization in various human disease states, Clin Chim Acta, V.82, N.1–2, p. 1–7, 1978 (abstract).

Courtright, L.J., Kuzell, W.C., Sparing effect of neurological deficit and trauma on the course of adjuvant arthritis in the rat, Ann Rheum Dis, V.24, N.4, p. 360–368, 1965 (abstract).

Cundliffe, E., Intracellular distribution of ribosomes and polyribosomes in bacillus megaterium, J Mol Biol, V.52, N.3, p. 467–481, 1970 (abstract).

Drexler, H., Zeiher, A.M., Meinzer, K., Just, H., Correction of endothelial dysfunction in coronary microcirculation of hypercholesterolaemic patients by L–arginine, Lancet, V.338, N.8782–8783, P. 1546–1550, 1991 (abstract).

Eich, R.F., Li, T., Lemon, D.D., Doherty, D.H., Curry, S.R., Aitken, J.F., Matthews, A.J., Johnson; K.A., Smith, R.D., Phillips, G.H., Jr. Olsen, J.S., Mechanism of NO–induced oxidation of myoglobin and hemoglobin, Biochemistry, V.35, N.22, p. 6979–6983, 1996 (abstract).

Entman, M.L. Smith, C.W., Postreperfusion inflammation: a model for a reaction to injury in cardiovascular disease, Cardiovasc Resc, V.28, N.9, p. 1301–11, 1994 (abstract).

Entman, M.L., Michael, L., Rossen, R.D., Dreyer, W.J., Anderson, D.C., Taylor A.A., Smith C.W., Inflammation in the course of early myocardial ischemia, FASEB J, V.5, N.11, p. 2529–2537, 1991 (abstract).

Feld, G.K., Evolution of diagnostic and interventional cardiac electrophysiology: a brief historical review, Am J Cardiol, V.84, N.9A, p. 115R–124R, 1999 (abstract).

Green, L.C., Wagner, D.A., Glogowski, J., Skipper, P.L., Wishnok, J.S., Tannenbaum, S.R., Analysis of nitrate, nitrite, and [15N] nitrate in biological fluids, Anal Biochem, V.126, N. 1, p. 131–138, 1982 (abstract).

Griswald, D.E., Hillegass, L.M., Hill, D.E., Egan, J.W., Smith, E.F., Method for quantification of myocardial infarction and inflammatory cell infiltration in rat cardiac tissue, J Pharmacol Methods, V.20, N.3, P.225–235, 1988 (abstract).

Hearse, D.J., Bolli, R., Reperfusion induced injury: manifestation, mechanisms, and clinical relevance, Cardiovasc Res, V.26, N.2, p. 101–108, 1992 (abstract).

Herrera, F., Adamson, R.H., Gallo, R.C., Uptake of transfer ribonucleic acid by normal and leukemic cells, Proc Natl Acad Sci USA, V.67, N.4, p. 1943–1950, 1970 (abstract).

Hibbs, J.B., Jr., Taintor, R.R., Vavrin, Z., Rachlin, E.M., Nitric oxide: a cytotoxic activated macrophage effector molecule, Biochem Biophys Res Commun, V.157, N.1, p. 87–94, 1988 (abstract).

Hoshida, S., Kuzuya, T., Nishida, M., Kim, Y., Kitabatake, A., Kamada, T., Tada, M., Attenuation of neutrophil function by inhibitors of arachidonate metabolism reduces the extent of canine myocardial infraction, V.63, N.10, o. 24E–28E, 1989 (abstract).

Hofer, H.W., Pette, D., The complex nature of phosphofructokinase—a nucleic acid containing enzyme, Life Sci, V.4, N.16, p. 1591–1596, 1965 (abstract).

Hui, S.W., Stewart, C.M., Carpenter, M.P., Stewart, T.P., Effects of cholesterol on lipid organization in human erythrocyte membrane, J Cell Biol, V.85, N.2, P283–291, 1980 (abstract).

Huot, A.E., Kruszyna, H., Kruszyana, R., Smith, R.P., Hacker, M.P., Formation of nitric oxide hemoglobin in erythrocytes co–cultured with alveolar macrophages taken from bleomycin treated rats, Biochem Biophys Res Commun, V.182, N.1, p. 151–157, 1992 (abstract).

Khawaja, J.A., Interaction of ribosomes and ribosomal subparticles with endoplasmic reticulum membranes in vitro: effect of spermine and magensium, Biochim Biophys Acta 1971, V.254, N.1, p. 117–128, 1971 (abstract).

Kellogg, E.W., Fridovich, I., Liposomes oxidation and erythrocyte lysis by enzymically generated superoxide and hydrogen peroxide, J Biol Chem, V.252, N.19, p. 6721–6728, 1977 (abstract).

Kosaka, H., Harada, N., Watanabe, M. Yoshihara, H., Katsuki, Y., Shiga, T., Synergistic stimulation of nitric oxide hemoglobin production in rats by recombinant interleukin 1 and tumor necrosis factor, Biochem Biophys Res Commun, V.189, N.1, P392–397, 1992 (abstract).

Lam, B.K., Gagnon, L., Austen, K.F., Soberman, R.J., The mechanism of leukotriene B4 export from human polymorphonuclear leukocytes, J Biol Chem, V.265, N.23, p. 13438–41, 1990 (abstract).

Leslie, C.C., Channon, J.Y., Anionic phospholipids stimulate an arachidonoyl–hydrolyzing phospholipase A2 from macrophages and reduce the calcium requirement for activity, Biochim Biophys Acat, V.1045, N.2, p. 261–270, 1990 (abstract).

Levine, L., Morgan, R.A., Lewis, R.A., Austen, K.F., Clark, D.A., Marfat, A., Corey, E.J., Radioimmunoassay of the leukotrienes of slow reacting substance of anaphylaxis, Proc Natl Acad Sci USA, V.78, N.12, p. 7692–7696, 1981 (abstract).

Lorenz, R.L. Boehlig, B., Udelhoven, W.M., Weber, P.C., Superior antiplatelet action of alternate day pulsed dosing versus split dose administration of aspirin, Am J Cardiol, V.64, N.18, p. 1185–1188, 1989 (abstract).

Lukacs, G.L., Kapus, A., Nanda, A., Romanek, R., Grinstein, S., Proton conductance of the plasma membrane: properties, regulation, and functional role, Am J Physiol, V.265, N.1 pt 1, P.C3–C14, 1993 (abstract).

Mainwaring, W.I., The effect of age on protein synthesis in mouse liver, Biochem J., V.113, N.5, p. 869–878, 1969 (abstract).

McCann, D.S., Tokarsky, J., Sorkin, R.P., Radioimmunoassay for plasma thromboxane B2, Clin Chem, V.27, N. 8, p. 1417–1420, 1981 (abstract).

Mechler, B., Vassalli, P., Membrane–bound ribosomes of myeloma cells. I. Preparation of free and membrane–bound ribosomal fractions. Assessment of the methods and properties of the ribosomes, J Cell Biol, V.67, N.1, p. 1–15, 1975 (abstract).

Moscat, J., Moreno, F., Herrera, C., Iglesias, S., Garcia–Barreno, P., Arachidonic acid releasing systems in pig aorta endothelial cells, Biochem Biophys Res Commun, V.139, N.3, p. 1098–1103, 1986 (abstract).

Mueller, B., Maass, B., Krause, W., Witt, W., Limitation of myocardial uperfused area and necrotic zone 24 and 7 days after coronary artery ligation in rats by the stable prostacyclin analogue iloprost, Prostaglandins Leukot Med, V.21, N.3, P331–340, 1986 (abstract).

Oddis, C.V., Simmons, R.L., Hattler, B.G., Finkel, M.S., cAMP enhances inducible nitric oxide synthase mRNA stability in cardiac myocytes, Am J Physiol, V.269, N.6 pt 2, p. H2044–2050, 1995 (abstract).

Osori e Castro, V.R., Ashwood, E.R., Wood, S.G., Vernon, L.P., Hemolysis of erythrocytes and fluorescence polarization changes elicited by peptide toxins, aliphatic alcohols, related glycols and benzylidence derivatives, Biochim Biophys Acta, V.1029, N.2, p. 252–258, 1990 (abstract).

Peng, H.B., Spiecker, M. Liao, J.K., Inductible nitric oxide: an autoregulatory feedback inhibitor of vascular inflammation, J Immunol, V.161, N.4, p. 1970–6, 1998 (abstract).

Rodionova, N.P., Shapot, V.S., Ribonucleic acids of the endoplasmic reticulum of animal cells, Biochem Biophys Acta, V.129, N.1, p. 206–209, 1966 (abstract).

Rothenberg, M., Johnson, G., Laughlin, C., Green, I., Cradock, J., Sarver, N, Cohen, J.S., Oligodeoxynucleotides as anti–sense inhibitors of gene expression: therapeutic implications, J Natl Cancer Inst, V.81, N.20, p. 1539–1544, 1989 (abstract).

Rybczynska, M., Csordas, A., Chain length–dependent interaction of free fatty acids with the erythrocyte membrane, Life Sci, V.44, N.9, p. 625–632, 1989 (abstract).

Salkowski, C.A., Detore, G., McNally, R., van Rooijen, N., Vogel, S.N., Regulation of inducible nitric oxide synthase messenger RNA expression and nitric oxide production by lipopolysaccaride in vivo: the roles of macrophages, endogenous IFN–gamma, and TNF receptor–1 mediated signaling, J Immunol, V.158, N.2, p. 905–912, 1997 (abstract).

Sato, Y., Kamo, S., Takahashi, T., Suzuki, Y., Mechanism of free radical–induced hemolysis of human erythrocytes: hemolysis by water–soluble radical initiator, Biochemistry, V.34, N.28, p. 8940–8949, 1995 (abstract).

Scott–Burden, T., Hawtrey, A.O., Preparation of ribosome–free membranes from rat liver microsomes by means of lithium chloride, Biochem J, V.115, N.5, p. 1063–1069, 1969 (abstract).

Sen, T., Ghosh, T.K., Chaudhuri, A.K., Glucose oxidase–induced lysis of erythrocytes, Indian J Exp Biol, V.33, N.1, p. 75–76, 1995 (abstract).

Shapot, V.S., Davidova, S.Y., Liporibonucleoprotein as an integral part of animal cell membranes, Prog Nucleic Acid Res Mol Biol, N.11, p. 81–101, 1971 (abstract).

Svendsen, J.H., Hansen, P.R., Ali, S., Baandrup, U., Haunso, S., Leucocyte depletion attenuates the early increase in myocardial capillary permeability to small hydrophilic solutes following and reperfusion, Cardiovasc Resc, V.27, N.7, p. 1288–1294, 1993 (abstract).

Tata, J.R., The formation, distribution and function of ribosomes and microsomal membranes during induced amphibian metamorphosis, Biochem J, V.105, N.2, p. 783–801, 1967 (abstract).

Tsunamoto, K., Todo, S., Imashuku, S., Separation of prostaglandins and thromboxane by two–dimensional thin–layer chromatography, J Chromatogr, V.417, N.2, p. 414–419, 1987 (abstract).

Vesterqvist, O., Measurements of the in vivo synthesis of thromboxane and prostacyclin in humans, Scand J Clin Lab Invest, V.48, N.5, p. 401–407, 1988 (abstract)

Wollny, T., Iacoviello, L., Buczko, W., de Gaetano, G., Donati, M.B., Prolongation of bleeding time by acute hemolysis in rats: a role for nitric oxide, Am J Physiol, V.272, N.6, pt 2, p. H2875–H2884, 1997 (abstract).

Yan, L., Vandivier, R.W., Suffredini, A.F., Danner, R.L., Human polymorphonuclear leukocytes lack detectable nitric oxide synthase activity, J Immunol, V.153, N.4, p. 1825–1834, 1994 (abstract).

Zhou, Q., Hellermann, G.R., Solomonson, L.P., Nitric Oxide release from resting human platelets, Thromb Res, V.77, N.1, p. 87–96, 1995 (abstract).

Zon, G., Oligonucleotide analogues as potential chemotherapeutic agents, Pharm Res, V.5, N.9, p. 539–549, 1988 (abstract).

* cited by examiner-

COMPOUND, COMPOSITION AND METHOD FOR THE TREATMENT OF INFLAMMATORY AND INFLAMMATORY-RELATED DISORDERS

FIELD OF THE INVENTION

The present invention concerns a compound and a pharmaceutical composition for the treatment of inflammation and diseases accompanied by inflammatory processes, in particular inflammatory processes which affect cellular membranes. The present invention also concerns therapeutic methods to ameliorate or prevent symptoms of inflammatory processes.

BACKGROUND OF THE INVENTION

Inflammatory Processes

Inflammation is generally accompanied by changes in the metabolism of arachidonic acid, metabolism of nitric oxide, and creation of free radicals. Anti-inflammatory non-steroid drugs (NSAIDS), such as aspirin, can block certain links of an inflammatory process, but these drugs cannot stabilize damaged cellular membranes, which makes their influence on an inflammatory process limited and insufficient.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is inevitably followed by an altered structure and penetrability of the cellular membrane. At the tissue and organ level, inflammation is indicated by pain, swelling, reddening, increased temperature, and a lost function in some cases. Inflammation begins with a sublethal damage and terminates either with a complete recovery or long-term tissue ruination. There is no recovery from an injury without an inflammation.

An immediate response to a tissue damage is realized via mediators, which are released due to the exocytosis or lysis of cells. The main inflammatory mediators are compounds of the kinine and fibrinolytic systems, the complement system, metabolites of arachidonic acid, vasoactive amines, and other chemical compounds. The chemical mediators of inflammation include: histamine, serotonin, prostaglandins, CGRP, nitric oxide, among others.

An important role in inflammations is played by various reactive oxygen-containing species. These compounds are synthesized when oxygen transforms them into very dangerous forms, producing free radicals, which are atoms and molecules with unpaired electrons. Different free radicals have different activity levels.

The launch of an inflammation is influenced by various exogenous and endogenous agents. Endogenous factors, namely, mediators, antigens, and autogens define the nature and type of the inflammatory reaction, especially its course in the zone of injury. In the case where a tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Inflammatory processes rely on the metabolism of arachidonic acid, which converts to prostaglandines (PG), tromboxanes (TX), and leukotrienes (LT). Prostaglandines, tromboxanes, and leukotrienes are the main participants of all inflammatory processes. There are two known ways of arachidonic acid cascade. The first way leads to the creation of prostaglandines $G_2$ and $H_2$. This process is catalyzed by prostaglandin-cyclooxygenase. Cyclooxygenase catalyzes the production of $PGA_2$, $PGE_2$, $PGD_2$, $PGF_{2\alpha}$, while tromboxane-synthesis with $PGH_2$ produces tromboxane $A_2$ ($TXA_2$).

The cascade of metamorphoses of arachidonic acid, which is a product of membrane and phospholypase $A_2$, is best known. Through its cyclogenase and lypoxygenase cascades, arachidonic acid turns into prostaglandins and leukotrienes, respectively. The cyclooxygenase way leads to the formation of two bio-active products: prostacycline ($PGI_2$) and thromboxane ($TXA_2$). These products are involved in many inflammatory effects: bronchoconstriction, vazodilation, vasoconstriction, platelet aggregation, analgesia, pyrexia, et al.

Another way of arachidonic acid metabolism with 5-lipoxygenase leads to the synthesis of leukotrienes: $LTA_4$, $LTB_4$, $LTC_4$, $LTD_4$, $LTE_4$, and $LTF_4$. These leukotrienes have a powerful anti-inflammatory and bronchoconstrictor action, and they play and important role in vascular penetrability. Besides, leukotrienes are known as potential chemotactic factors; they increase the migration of WBC and have a great influence on the slow-releasing substance of anafilaxis (SRS-A).

Prostaglandines can play an important role in the development of systemic inflammatory reactions. In rheumatic arthritis, large quantities of PG and LT in the synovial liquid support the development of an inflammatory process and demineralization of bone tissue surrounding joints. Leukotrienes are known to be the main patho-physiological mediators of inflammatory reactions. They influence, to a greater degree than prostaglandines, the penetrability of vessels and the adhesion of leukocytes to vessel walls as well as the development of edema.

Prostaglandines effectively regulate the aggregation of platelets. $PGE_1$ is a powerful inhibitor of platelets aggregation, while $PGE_2$, which is normally released from platelets, stimulates this process. However, the most important role in blood coagulability is played by $PGI_2$, or prostacycline, which is synthesized in blood vessel walls by arachidonic acid. It is the most powerful inhibitor of platelets aggregation, which has vasodilator properties. Thromboxane, which is synthesized in platelets, has an opposite action.

When endothelium is damaged, the adhesion of platelets with subendothelium tissue and the aggregation of platelets is initiated. The main role in this process is played by thromboxane $A_2$. Prostaglandin $I_2$, on the contrary, inhibits the aggregation of platelets. Therefore, the proportion of $PGI_2$ and $TXA_2$ is crucial for the process of coagulation.

Further, a special role in the process of recovery from inflammation is played by nitrogen oxide (NO). This gas easily penetrates in different organs and tissues and, as a free radical, has a powerful reactivity. Nitrogen oxide is a potent vasodilator, neurotransmitter, and inflammatory mediator, which plays a significant role in asthmatic inflammation.

Nitrogen oxide is produced endogenously by L-arginine amino acid and NO-synthetase. There are three known forms of NO-synthetase, two of which are constituent, and one inducible. The inducible NO-synthetase, which is expressed in the epithelium cells, quickly increases its activity when anti-inflammatory cytokines (such as interleukin 1 beta (IL-1beta) and tumor necrosis factor (TNF-alfa) are released.

Nitrogen oxide has both positive and negative properties with respect to an inflammatory reaction. One important and potentially positive property is its ability to relax the smooth bronchial muscle, which results in bronchodilation. Its negative properties include the ability to help the inflammatory process by increasing chemotaxis neutrophils, monocytes, and oesinofils with the help of the guasine-monophosphate-dependent mechanism. It is believed that nitrogen oxide inhibits adhesion of leukocytes to vascular endothelium and bronchial epithelium.

NO plays an important biological role in defining basal vascular tonus, regulating contractions of myocardium, and modulating the interaction between thrombocytes and vascular walls (Zhou Q., Hellermann G. R., Solomonson L. P., Nitric oxide release from resting human platelets, Thromb.Res., 1;77(1):87–86; 1995). The role of thrombocyte activation in the pathogenesis of various thrombovascular conditions in humans and evidence about decreased NO-mediated effects in hypertension (Calver A., Collier J., Moncada S., Vallance P., Effect of local intra-arterial NG-monomethyl-L-arginin in patients with hypertension: the nitric oxide dilator mechanism appears abnormal, J.Hypertens., 10(9):1025–1031; 1990), diabetes (Calver A., Collier J., Valance P., Inhibition and stimulation of nitric oxide synthesis in the human foream arterial bed of patients with insulin-dependent diabet, J.Clin.Invest, 90(6):2548–2554; 1992), and artherosclerosis (Drexler H., Zeiher A. M., Meinzer K., Just H., Correction of endotelial dysfunction in coronary microcirculation of hypercholesterolaemic patient by L-arginine, Lancet., 21–28; 338 (8782–8783); 1546–1550; 1991) suggests that drugs which increase the activity of NO-synthetase may effectively be used in treatment of patients. Human thrombocytes are capable of synthesizing nitric oxide. Large quantities of nitric oxide, for example, in the cells of endothelium, may be produced by intact thrombocytes, as well as by stimulated thrombocytes. Hence, nitric oxide of thrombocyte origin plays an important role in the support of vascular homeostasis and other NO-sensitive processes. (Zhou et al.,1995).

Beside some common features, inflammatory processes in each individual case have certain distinctions related to the peculiarities of functioning of the body organ and to the factors which caused the impairment: i.e., viruses, microorganisms, injuries, poisoning, etc.

For example, one of the common mechanisms of heart diseases, including acute infarct myocarditis, is a malfunction of the structure and function of the membrane of heart cells. As a result, the synthesis of leukotrienes, tromboxanes, etc., which have coronoconstrictor, arrythmogenic, hemoatractive and pro-aggregate action, increases (Bangham A. D., Hill M. W., Miller N., Preparation and use of liposom as model of biological membranes, Methods in Membrane Biology, Acad. Press, V.1, N. Y., P.1–68, 1974).

Another important factor in the pathogenesis of heart impairments is the coronoconstrictor and hemoattractive (with regard to neutrofiles) action of lipoxygenase derivatives $LTC_4$, $LTD_4$, $LTB_4$ (Hoshida S, Kuzuya T., Nishida M., et al., Amer.J.Cardiol, 7; 63(10): 24E–2E; 1989; Lam B. K., Gagnon L., Austen K. F. et al., J.Biol.Chem., 15; 265(23): 13438–1341; 1990; Svendsen J. N., Hansen P. R., Ali S. et al., Cardiovasc.Res., 27(7): 1288–1294; 1993). Substances which can block this process can in turn reduce the size of necrosis at acute myocardial infarction and, therefore, significantly decrease the lethality in difficult cases of heart disease, such as gross myocardial infarction. At the same time, such substances can stabilize the membranes of heart cells. In addition, it is known that coronoconstrictor and hemoattractive effects during infarct are accompanied by an increased aggregation of platelets. Therefore, blocking this process also leads to a decrease of the size of impairment.

Further, disorders of the aggregate state of blood play an important role in the pathogenesis of various diseases. This is especially apparent in the pathogenesis of thrombovascular conditions in humans. It is known that a malfunction in the thrombo-vascular link of homeostasis is a key factor leading to disorders of the aggregate state of blood, by causing changes in the rheological properties of blood and triggering the formation of internal vascular aggregates. Thrombocyte-related injuries lead to failures in microcirculation processes, which result in shortages of blood inflow to the tissue. At the initial stage of the formation of blood clots, platelets become activated and further undergo adhesion to the injured endothelium. Later on, they aggregate and an initial thrombocytic blood clot is formed.

Today, there is enough evidence of a close relation between inflammations, disorders in the aggregate state of blood, and cardio-vascular conditions (Anderson J. L. Cariqist J. L., et al., Evaluation of C-reactive protein an inflammatory marker, and infectious serology as risk factors for coronary artery disease and myocardial infarction, J.Am. Coll. Card., 32: 35–41; 1998).

Role of Cell Membranes in Inflammatory Processes

The functions of cell membranes and their relation to inflammatory processes has been documented. It is known that the plasmatic cellular membrane occupies a special place among the other membrane structures and performs such important functions as barrier and transportation, provides a contact with the outside environment for the cell, participates in the regulation of cellular homeostasis, supports signal mechanisms of this regulation, and defines the cell's individuality and wholeness. The structural organization, dynamics, and functions of erythrocytal membranes and various hemolysis patterns, such as osmotic, oxide, immune (induced by hemolytic viruses, toxins, complement), detergent hemolysis, photohemolysis, etc., are well studied (see, e.g., Bashford C. L., Alder G. M., Menestrina G.,et al., Membrane damage by hemolytic viruses, toxins, complement, and other cytotoxic agents. A common mechanism blocked by divalent cation. J. Biol. Chem., 15; 261(20): 9300–9308, 1986; Osorie e Castro V. R., Ashwood E. R., Wood S. G., Vernon L. P., Hemolysis of erythrocytes and fluorescence polarization changes elicited by peptide toxins, aliphatic alcohols, related glycols and benzylidene derivatives, Biochim. Biophys. Acta., 16; 1029(2): 252–258; 1990).

It was demonstrated that pH variation in the outside environment upsets the balance of forces influencing the membrane, which leads to structural changes and changes of the aggregation degree of membrane proteins. Two types of membrane structural changes are distinguished: those caused by pH variation in the range 7.0–6.0, and those for pH levels below 4.5 (Zavodnik I. B., Pileckaya T. P., Acid lysis of human erythrocytes, Biophizika., V.42, N.5, P.1106–1112, 1997). In the latter case, the membrane becomes destabilized and erythrocytal lysis follows. It is known that at pH 4.7, pores are formed in glycocalyx erythrocytal membranes (Arvinte T., Cudd A., Schulz B., Nicolau C., Biochim. Biophys. Acta., 19; 981(1): 61; 1989). In particular, decreased pH levels of the environment change the confirmation, package type, and mobility of phospholipids in model membranes. Thus, aggregation of membrane proteins, denatured due to a decreased pH, is the reason for membrane damages and acid lysis in erythrocytes.

The pattern of erythrocytal hemolysis by HCl was proposed based on the cooperative protonation of some center located in stroma or on the membrane of erythrocyte with a subsequent creation of pores, sufficient to release hemoglobin. By studying the mechanism and pattern of the acid hemolysis process, information about the structural organization of the membrane and membrane-stabilizing actions can be obtained.

The best known endogenous stabilizers of hemolysis in erythrocytes (osmotic hemolysis is the best-studied) are albumin of blood plasma, metallic ions K+, Na+, $Mg^{2+}$ and, especially, $Ca^{2+}$, which modulate the canals of plasmatic erythrocytal membranes, possibly including the proton canal (Anderson D. R., Davis J. L., Carraway K. L., Calcium-promoted changes of the human erythrocyte membrane. Involvement of spectrin, transglutaminase, and a membrane-bound protease. J. Biol. Chem., 10; 252(19): 6617–6623, 1977), cholesterol adsorbed on the surface of erythrocytes (Hui S. W., Stewart C. M., Carpenter M. P., Stewart T. P. Effects of cholesterol on lipid organization in human erythrocyte membrane, J. Cell. Biol., 85(2): 283–291; 1980), and polyamines, which bind with the fatty-acid residues of membrane phospholipids (Rennert O. M., Shukla J. B., Polyamines in health and disease Advances in Polyamine research, Raven Press, V.2, N.Y, P.195–21, 1978). The best known activators of endogenous hemolysis in erythrocytes are long-chain fatty acids (Rybszynska M., Csordas A, Chain length-dependent interaction of free fatty acids with the erythrocyte membrane, Life Sci., 44(9): 625–682; 1989), and especially free radicals of oxygen and nitrogen (Sato Y., Kamato S., Takahashi T. et al., Mechanism of free radical-induced hemolysis of human erythrocytes: hemolysis by water-soluble radical initiator. 18; 34(28): 8940–8949; 1955; Sen T.,Ghosh T. K., Chaudhuri A. K. Glucose oxidase-induced lysis of erythrocytes. J,Exp.Biol., 33;(1): 75–76; 1995; Wollny T., Yacoviello L. Propogation of bleeding time by acute hemolysis in rats: a role for nitric oxide. Am. J. Physiol. 272(6): 2875–2884; 1997).

In summary, there is evidence to suggest that the structure of the membrane is altered during inflammatory processes. However, the model of membrane damage in the inflammatory process has not been used for screening drugs and treating or preventing inflammation and inflammatory-related disorders.

Present Drugs Unsatisfactory

The present anti-inflammatory drugs are unsatisfactory because the difficult and various biochemical reactions involved in inflammations and the lack of reliable information about inflammatory pathogenesis complicate the experimental choice of pharmacological compounds capable to regulate inflammation. Thus, drugs are selected to have an effect on individual components of an inflammation. So far, there is no drug able to regulate most of the components of any inflammatory reaction.

Most of the known non-steroid anti-inflammatory drugs (NSAIDS) selectively influence certain phases of this pathological process. First, they influence the penetrability of blood vessels, which is often altered in acute inflammations, and various cell reactions, which are common for chronic inflammations. Also, many NSAIDS influence metabolism through the mechanism of free radicals.

The initial screening of anti-inflammation processes typically uses three groups of methods. First, the influence of drugs on easily-identifiable inflammatory symptoms is studied. These include swelling, hyperemia, necrosis, etc. A more advanced analysis includes experimental therapy methods, using model arthritis, carditis, etc., which are similar to human ailments. The third stage involves analysis of how the drug influences certain metabolic ways.

After the metabolism of arachidonic acid was studied in detail, many anti-inflammatory compounds, whose action was to regulate the formation of such metabolic products, were proposed. In most cases, such drugs act as inhibitors of the metabolic enzymes of arachidonic acid. One example is the anti-inflammatory pharmacological combination of cyclooxygenase 2 inhibitor and leukotriene A.sub.4 hydrolase inhibitor (Isakson, P. C., Anderson G. D., Gregory, S. A., Treatment of inflammation and inflammation-related disorders with a combination of a cyclooxygenase-2 inhibitor and a leukotriene A.sub.4 hydrolase inhibitor, U.S. Pat. No. 5,990,148, November 1999). A similar approach was proposed on the basis of analogues of pyrimidines, a component of nucleic acids (Connor D. T., Kostlan C. R., Unangst P.C., 2-heterocyclic-5-hydroxy-1,3-pyrimidines useful as antiinflammatory agents, U.S. Pat. No. 5,240,929, August 1993). Since these compounds are the inhibitors of key metabolic ferments of arachidonic acid, 5-lipoxygenase and cyclooxygenase, the authors suggested their use as anti-inflammatory drugs suitable for treatment of a wide range of diseases, from allergenic conditions and rheumatoid arthritis to artherosclerosis and myocardial infarction. Other researchers recommended prostacyclin analogues for treatment of thrombocyte aggregation and bronchoconstriction (Haslanger M. F., Prostacyclin analogs and their use in inhibition of arachidonic acid-induced platelet aggregation and bronchoconstriction, U.S. Pat. No. 4,192,891, March 1980).

However, since an inflammatory process initiates many different metabolic cascades, the use of inhibitors or metabolic analogues of arachidonic acid does not allow to balance all such reactions and, hence, cannot regulate the complex inflammatory process in a satisfactory manner.

Further, aspirin, which has been used in applied medicine for a long time, has also been proposed since it can block metabolic ferments of arachidonic acid. Inhibitors of prostaglandines, such as aspirin, quite effectively influence the inflammatory processes. For this reason, they are successfully used in clinics for the treatment of rheumatoid arthritis, osteoarthritis, and other similar inflammatory processes. Aspirin also has anti-coagulation properties, since it inhibits the synthesis of $TXA_2$, and it influences at least partially the synthesis of $PGI_2$. A daily dose of 3 g of aspirin is commonly used for prevention of stenocardia, as a post-infarct and post-insult treatment, or for patients with a high risk of cardio-vascular conditions.

However, studies on the synthesis of $TXA_2$ and $PGI_2$ in vivo have shown that peroral administration of aspirin decreases the secretion of $PGI_2$ only for 2–3 hours, while the secretion of thromboxane is halted for 10 days (Vesterqvist O., Measurements of the in vivo synthesis of thromboxane and prostacyclin in humans, Scand. J. Clin. Lab. Invest. 48(5): 401–407; 1988). This author, as well as others (see, e.g., Lorenz R. L., Boehlin B., Uedelhoven M. W., Weber P. C., Superior antiplatelet action of alternate day pulsed dosing versus split dose administration of aspirin, Am. J. Cardiol. 15; 64(18): 1185–1188; 1989), not only show the difficulties in administering the right dose of aspirin, but also provide and experimental ground for the frequent side effects caused by aspirin during its long-term use.

Specifically, aspirin and other non-steroid anti-inflammatory drugs may be the cause of anaphylactoid reactions in sensitive individuals. The mechanism of these reactions is dose-dependent toxic-idiosyncratic, not immunologic. Also, aspirin is the most common cause of accidental poisoning. Children, treated by aspirin before poisoning, are also at great risk. Aspirin overdose, which occurs frequently, is difficult to correct. The effective aspirin dose for many diseases, including rheumatoid arthrtis, constitutes 3–6.5 mg per day, which leads to irritations of the gastro-intestinal tract. Patients with gastro-intestinal conditions do not tolerate aspirin. Aspirin also causes erosion, bleeding stomach ulcers, diarrhea, and duodenum ulcers. Further, aspirin is commonly used in treatment for its anti-thrombocytic action, but it is badly tolerated and causes side-effects when taken for a long period of time. In addition, by inhibiting non-selectively cyclooxygenesis, aspirin interferes with the synthesis of thromboxane, which is a powerful aggregant and vasoconstrictor, and may also lead to decreased levels of prostacycline, which is both anti-aggregant and vasodilator.

All these negative side-effects of aspirin and other NSAIDS motivate the search for new drugs which would have anti-inflammatory properties, but which are non-toxic in a wide range of concentration, have no side effects during a long-term use, and are capable of preventing and terminating inflammatory processes.

Pharmaceutical Use of Nucleic Acids

Nucleic acids are commonly used in pharmacology (Rothenberg M., Jonson G., Laughlin C. et al. Oligodeoxynucleotides as anti-sense inhibitors of gene expression: therapeutic implications, J. Natl. Cancer Inst., 18; 81(20): 1539–1544; 1989; Zon G., Oligonucleotides analogues as potential chemotherapeutic agents, Pharm. Res., 5; (9): 539–549; 1988). However, pharmaceutical uses for nucleic acids have not included inflammatory or inflammatory-related disorders. For example, Anderson et al., proposes the method of modulating the effects of cytomegalovirus infections with the help of an oligonucleotide, which binds with mRNA of cytomegalovirus, for treatment of cytomegalovirus infections in humans (Anderson K., Draper K., Baker B., Oligonucleotides for modulating the effects of cytomegalovirus infections, U.S. Pat. No. 5,442,049, Aug. 15, 1995). On the basis of a specific nucleic acid, which encodes the succession of 3'non-translated sector of protein kinase C, Boggs et al. propose a method for diagnosis and treatment of conditions, which are associated with protein kinase C alpha (Boggs R. T., Dean. N. M., Nucleic acid sequences encoding protein kinase C and antisense inhibition of expression thereof, U.S. Pat. No. 5,681,747, October 1997). Also, Yano et al. patented a DNA compound obtained from *Mycobouterium bovis* and *Bacillus subtilis* for treatment of stomach ulcers (Yano O., Kitano T., Method for the treatment of digestive ulcers, U.S. Pat. No. 4,657,896, April 1987).

In particular, it is known that ribonucleic acid (RNA), products of its partial hydrolysis, and synthetic polyribonucleotides have a wide range of bioactivity (Kordyum V. A., Kirilova V. S., Likhachova L. I., Biological action of exogenous nucleic acids, Visnyk ASC USSR, V.41, N.6, P.67–78, 1977). They activate protein synthesis in cells (Sved S. C., The metabolism of exogenous ribonucleic acids injected into mice, Canad.J.Biochem.,V.43, N.7, P.949, 1965) and have anti-tumor activity (Niu M. C., Effect of ribonucleic acid on mouse acids cells, Sciens., N.131, P.1321, 1960). RNA can increase antibody generation and decrease the inductive phase of antibody genesis (Johnson A. G., Schmidtke I., Merrit K. et at., Enhancement of antibody formation by nucleic acids and their derivatives, in Nucleic acid in immunology, Berlin, P.379, 1968; Merrit K., Johnson A. G., Studies on the adjuvant of bacterial endotoxins on antibody formation, 6. Enhancement of antibody formation by nucleic acids, J.Immunol., V.94, N.3, P.416, 1965; Brown W., Nakono M., Influence of oligodeoxyribonucleotides on early events in antibody formation, Proc. Soc. Exper. Biol. Med., 5, V.119, N.3, P.701, 1967). It was shown that certain increased or decreased immunologic indicators normalize under the influence of RNA. In the first place, this applies to T-lymphocytes, cooperation of T- and B-lymphocytes, activation of macrophage function, etc.

Further, exogenous RNA is used for the DNA synthesis in dividing cells and for the RNA synthesis in metabolizing cells. It was also determined that 2 hours after the introduction, exogenous RNA was included in the RNA of lymphocytes and macrophages (Enesco N. E., Fate of 14C-RNA infected into mice, Exper. Cell Res., V.42, N.3, P.640, 1966). Evidence suggests that yeast tRNA can be included into cells in the form of intact molecules (Herrera F., Adamson R. H., Gallo R. C., Uptake of transfer ribonucleic acid by normal and leucemic cells, Proc.Nat.Acad.Sci.USA, 67(4): 1943–1950; 1970).

It was determined by analytical methods that RNA is present in practically all membranes of animal cells (membranes of endoplasmic reticulum, mitochondrial, nucleic, and plasmatic membranes). Its content, depending on the type of tissue and on the method of membrane isolation, varies between 0.5 and 4% of the dry weight of the membrane. Experimental results show that special membrane RNA exists in isolated membranes (Shapot V. S., Davidova S. Y., Liponucleoprotein as an integral part of animal cell membrans. Prog. Nucleic Acid Res. 11: 81–101; 1971; Rodionova N. P., Shapot V. S. Ribonucleic acid of the endoplasmatic reticulum of animal cells. Biochim et Biophis Acta, 24; 129(1); 206–209; 1966). The functions of membrane RNA are not fully understood.

The functions of membrane RNA in ribosome have been better studied. (Cundliffe E., Intracellular distribution of ribosoms and poliribosomes in Bacillus megaterriium. J.Mol.Biol., 28; 52(3): 467–481; 1970) Ribosomal RNA is contained in bacterial membranes, in the outer membranes of nuclei, inner and outer membranes of mitochondria, inner membrane of the Goldgi apparatus, which adjoins the plasmatic membrane, in the rugged endoplasmic reticulum, in different tissues in animals, humans, plants, microorganisms, and protozoa. It is possible that membrane glycolipids and glycoproteins, which contain N-acetylneuraminic acid, are involved in the formation of binding sites of ribosomal RNA in ribosomes, since membranes which are treated by neuronidase lose the ability to bind ribosomes. (Scott-Burden T., Hawtrey A. O., Preparation of ribosome free membranes from rat liver microsomes by means of lithium chloride. Biochem. J. 115(5): 1063–1069; 1969. Further, it is possible that binding sites of ribosomes and membranes are activated by the sexual hormones, and cancerogens damage this physiological mechanism. This conclusion is supported by decreased levels of membrane-bound RNA in the process of aging (Mainwaring W. J. The effect of age on protein synthesis in mouse liver. Biochem J. 113(5): 869–878; 1969) and after castration of animals (Tata J. R., The formation, distribution and function of ribosomes and microsomal membranes during induced amphibian metamorphosis. Biochem J. 105 (2): 783–801, 1967). Extraction of spermine from a membrane leads to a separation of bound RNA from the membrane (Khawaja J. A. Interaction of ribosomes and ribosomal subparticles with endoplasmic reticulum membranes in vitro: effect of spermine and magnesium. Biochim. Biophis. Acta., 29; 254(1): 117–128); 1971). When membranes are treated with RNA of native small ribosomes of myeloma cells, they separate from the membranes, while large native subunits of ribosomes remain bound with the membranes (Mechler B.,Vassalli P., Membrane-bound ribosomes of myeloma cells.I.Preparation of free and membrane-bound ribosomal fractions. Assessment of the methods and properties of ribosomes. J.Cell.Biol. 67(1): 1–15; 1975. Also, the nucleotide components of various membrane enzymes, for example, polyA-RNA enzyme of phosphofructokinase, constitute a possible pool of membrane RNA (Hofer H. W., Pette D. The complex nature of phosphofructokinase—a nucleic acid countaining enzyme, Life Sci. 4(16): 1591–1596; 1965).

However, nucleic acids, and in particular RNA, and compositions containing the same, have not been used to treat or prevent inflammatory or inflammatory-related disorders. In particular, most of the studies above rely on experiments in vitro. Further, none of these methods is directed to treating or preventing an inflammation or inflammatory-related disorder.

Need for New Drug

In view of the above, there is a need for new anti-inflammatory drugs which would regulate disorders of the aggregate state of blood and would have less negative effects than aspirin and other NSAIDS. In particular, since an inflammatory process in the initial stage is followed by alterations in the structure and functions of the membrane in the many cells involved in the inflammatory process, drugs are needed which, not only regulate all the components of an inflammatory metabolic cascade, but also stabilize membrane structures and functions in the involved cells. In particular, since the traditional therapy has little effectiveness in extensive infarcts, which are complicated by the cardiogen shock, there is a need for new drugs capable of stopping the destruction of cardiomyocytes.

SUMMARY OF THE INVENTION

The present invention offers a compound, a pharmaceutical composition and a method for the treatment or prevention of inflammation and diseases accompanied by inflammatory processes. The compound is an active ingredient consisting of RNA, in particular RNA extracted from yeast. Yeast RNA is a heterogenous compound of low-polymeric RNA, which comprises various quantities of nucleotides, nucleotide polymers, and usually 5 to 25 nucleotides. Oligonucleotides and transport RNA with a great number of minor bases prevail in yeast RNA.

Since one of the common features of all inflammatory processes at a molecular level is altered penetrability and structure of membrane, the present invention was made using a method of selecting drugs based on their ability to stabilize cellular membrane in inflammations. Thus, by analyzing destructive mechanisms induced by various factors in plasmatic membranes and learning about the structural elements of their interaction, which provide the optimal organization of a cell, it is possible to select drugs having membrane-stabilizing action for applied medicine. Specifically, it has now been established that, since membranes contain low-molecular RNA which probably plays a membrane-stabilizing role, introduction into the body of exogenous low-molecular RNA leads to stabilization of disturbed membranes, such as, for example, membranes of cells involved in inflammatory processes.

Stabilization of the cell membrane by the compound of the present invention leads to the normalization of arachidonic acid metabolism and nitric oxide metabolism, which have a powerful anti-inflammatory action and are the main participants of all inflammatory processes, for example, rheumatoid arthritis, osteoarthritis, allergies (such as asthma), and other inflammatory conditions, such as pain, swelling, fever, psoriasis, inflammatory bowel disease, gastrointestinal ulcers, cardiovascular conditions, including ischemic heart disease and atherosclerosis, partial brain damage caused by stroke, skin conditions (eczema, sunburn, acne), leukotriene-mediated inflammatory diseases of lungs, kidneys, gastrointestinal tract, skin, prostatitis, and paradontosis.

The yeast RNA is effective in decreasing the activity of iNOS in the course of an auto-immune process, both during its initiation and in the chronic stage. This property allows the usage of yeast RNA in pathological conditions which are accompanied by iNOS induction: diabetes, tumor, hepatitis, infections, neuro-degenerate diseases (Parkinson's disease, Alzheimer's disease, multiple sclerosis, encephalitis), and others.

In addition, the use of natural molecules of nucleic acids, such as the compound of the present invention, in large concentrations as pharmacological compounds causes no or little side effects, especially taking into account the fact that this compound constantly enters human and animal bodies with food.

Further, the present invention offers a method for the treatment of inflammation or inflammatory-related disorder comprising administering to a mammal in need of such treatment an amount effective to ameliorate the symptoms of inflammation or inflammatory-related disorder of ribonucleic acid and a pharmaceutically acceptable vehicle, carrier, or diluent.

Still further, the present invention offers a method of stabilizing damaged cellular membranes which comprises administering to a mammal having damaged cellular membranes an amount effective to stabilize said damaged cellular membranes of ribonucleic acid and a pharmaceutically acceptable vehicle, carrier, or diluent.

Still further, the present invention offers a method of normalization of NO-synthetase ability in a mammal which comprises administering to a mammal in need of such treatment an amount effective to normalize NO-synthetase ability in the mammal of ribonucleic acid and a pharmaceutically acceptable vehicle, carrier, or diluent.

Still further, the present invention offers a method of inhibiting oxidation of components of cell membranes of a mammal, which comprises administering to a mammal in need of such treatment an amount effective to inhibit oxidation of components of cell membranes of the mammal of ribonucleic acid and a pharmaceutically acceptable vehicle, carrier, or diluent.

Still further, the present invention offers a method of inhibiting thrombocyte aggregation, which comprises administering to a mammal in need of such treatment an amount effective to inhibit thrombocyte aggregation of ribonucleic acid and a pharmaceutically acceptable vehicle, carrier, or diluent.

Also, the present invention offers a compound consisting of ribonucleic acid extracted from yeast, for example a *Saccharomyces cerevisiae* or a *Candida utilis*. Preferably, the ribonucleic acid has a nitrogen content of more than 14.5% by weight and a phosphorus content of more than 8.5% by weight, more preferably a nitrogen content of more than 14.7% by weight and a phosphorus content of more than 8.6% by weight, even more preferably a nitrogen content of more than 15.0% by weight and a phosphorus content of more than 9.0% by weight.

Further, the present invention offers a pharmaceutical composition for the treatment or the prevention of inflammation or inflammatory-related disorder, comprising ribonucleic acid and a pharmaceutically acceptable vehicle, carrier, or diluent.

DETAILED DESCRIPTION OF THE INVENTION

A complex analysis of known nucleic acids was carried out using various in vitro and in vivo models. The models were chosen to correspond to certain types of inflammatory processes, both of common and immunologic origin. In the tests, the effects of ribonucleic acid (RNA), in particular yeast RNA, was compared to the effects of existing anti-inflammatory drugs over a wide range of anti-inflammatory activities.

Summary of Experimental Models and Results

1. Model of Thrombocyte Aggregation in Vitro

An initial screening of exogenous nucleic acids was conducted in vitro on the model of aggregation of human thrombocytes induced by arachidonic acid (Born L. V. R. The aggregation of blood platelets by difosfate and its reversal, Nature, V.94, P.327, 1962). Exogenous DNA and RNA from prokaryotes and eukaryotes were analyzed. We used aspirin as representative of a standard anti-inflammatory drug.

It was demonstrated that aspirin inhibited the aggregation of thrombocytes induced by arachidonic acid to a certain level. Desoxyribonucleic acid obtained from chicken erythrocytes (DNA-CE) produced by "Reanal" (Hungary), inhibited thrombocytic aggagation within the range of aspirin. Further, DNA from cattle thymus (DNA-CT) produced by "Reanal" (Hungary), and transport RNA of E. coli (tRNA) produced by "Serva" (USA) inhibited aggregation of the induced thrombocytes almost twice. The highest inhibiting effect was demonstrated by total yeast RNA, which dramatically inhibited thrombocytic aggregation in a wide range of concentrations. Inhibition of thrombocytic aggregation by yeast RNA depended on the form (acid or its sodium salt), purity, and presence of protein. RNA-F with protein admixtures was less effective by a third. The sodium salt of yeast RNA-PN in high concentration was only half as effective, and did not act in low concentration.

Since the model of aggregation of thrombocytes induced by arachidonic acid is recognized for the selection of anti-inflammatory drugs, the results of this comparative test showed that nucleic acids, and especially RNA, in particular, yeast RNA, have pronounced anti-inflammatory properties.

2. Model of Acid Resistance of Erythrocyte Membranes in Vitro

Based on the recognition that destabilization of cellular membranes is the main indication of an inflammatory process, we used the model of acid resistance of erythrocyte membranes in vitro for the screening of membrane-protecting, and thus, anti-inflammatory properties of the drugs. We chose rat erythrocytes to study the immune-stabilizing action of exogenous nucleic acids. We analyzed the reactions of erythrocytic membranes to the destructive influence of nitric oxide. We estimated the membrane-stabilizing action of exogenous nucleic acids and damaging actions of endogenous and exogenous nitrite anion by calculating the acid resistance of erythrocytes according to the kinetic method (Terskov I. A., Hittelzon I. I., Chemical (acid) erythrogram method, Biophizika, 2(2): 259–266; 1957). The main idea of the method is to determine historical changes in the number of cells, which eventually become hemolyzed under the influence of weak acids. The lysis of erythrocytes in acid environment undergoes three stages: penetration of hydrogen ions (protons, $H^+$) through the plasmatic membrane of erythrocytes, protonation of hemoglobin and membrane proteins, and, as a result, osmotic destruction of erythrocytes.

Using this method, we estimated the influence of exogenous nucleic acids on the kinetics of the penetration of protons through the erythrocytic plasmatic membrane, which depends on the membrane's nature. The speed of proton penetration in the cellular cytosol depends to a great extend on the oxidation status of the lipid component (Kellogg E. W., Fridovich I., Liposome oxidation and erythrocyte lysis by enzymically generated superoxide and hydrogen peroxide J. Biol. Chem. 10; 252(19): 6721–4728; 1977) and protein component, especially, the band 3 oxidation of plasmatic membranes and is defined by the activity $[H^+]$-ATP-ase, and the activity of various exchangers (Sato Y., Kamo S., Takahashi T., Suzuki Y., Mechanism of free radical-induced hemolysis of human erythrocytes: hemolysis by water-soluble radical initiator, Biochemistry, 18; 34(28): 8940–8949; 1995; Lukacs G. L., Kapus A., Nanda A. et al, Proton conductance of the plasma membrane: properties, regulation, and functional role, Am. J. Physiol, 265(1 Pt 1): C3–C14; 1993).

Acid erythrograms were recorded by the kinetic method. In the in vitro tests, acid erythrograms were recorded in the presence of sodium nitrite (the damaging agent) and different concentrations of exogenous nucleic acids.

The in vitro tests, which used the oxide damage model of erythrocytes by nitrite anion, a stable metabolite of nitric oxide, demonstrated stabilizing and membrane-protector action of exogenous nucleic acids.

On the model of acid resistance of erythrocytic membranes, we tested the same set of preparations as in the model of thrombocytic aggregation.

Yeast RNA preparations demonstrated membrane-protecting properties in a wide range of concentrations. A more detailed analysis showed that the membrane-protector action of yeast RNA depends on their form (acid or sodium salt), purity, and the presence of protein. Well-purified ribonucleic acid RNA-P, whose erythmograms in the concentrations 10 and 100 $\mu$kg corresponded to the norm, showed the highest effectiveness. Sodium salt of yeast RNA-PN was less effective, especially in the concentration 10 $\mu$kg. Protein admixtures in RNA-F resulted in a complete loss of the membrane-stabilizing action. Other preparations, tRNA, DNA-CT, and DNA-EC destabilized erythrocyte membranes at the tested concentrations, which means that they cannot be used as anti-inflammatory drugs as advantageously despite their anti-inflammatory properties demonstrated on other models.

3. Model of Erythrocytal Auto-Immune Reaction in Rats

We used the model of acid injury of erythrocytal plasmatic membranes to study the membrane-stabilizing action of exogenous nucleic acids. Acid damages to the protein and lipid components of erythrocytal plasmatic membranes were tested in vivo in the process of development of an auto-immune reaction (adjuvant arthritis). The biosynthesis of nitric oxide, which is an active oxidizing agent, became activated and, especially, hemoglobin of erythrocytes (Eich R. F., Li T., Lemon D. D. Mechanism of NO-induced oxidation of myoglobin and hemoglobin. Biochemistry, 4; 35(22): 6976–6983; 1966; Huot A. E., Kruszyna H., Kruszyna R. et al., Formation of nitric oxide hemoglobin in erythrocytes co-cultured with alveolar macrophages taken from bleomycin-treated rats. Biochem.-Biophys. Res. Commun., 15; 182(1); 151–158; 1992; Kosaka H., Harada N., Watanabe M. et al. Synergistic stimulation of nitric oxide hemoglobin production in rats by recombinant interleukin 1 and tumor necrosis factor. Biochem. Byophis. Res. Commun. 30; 189(1): 392–398; 1992). Nitric oxide, as well as hydrogen peroxide, plays a crucial role in the damage to cells, including blood cells, in the process of development of autoimmune reactions. The anti-inflammatory cytokines (gamma-interferon, IL-1) induce expression of the inducible isoform of NO-synthetase (iNOS).

We studied changes in the activity of NOS in rat blood in the development of autoimmune reaction (adjuvant arthritis) in order to evaluate the preparation's immune-modulating effect and to obtain information about possible levels of one of the most active oxidizing hemolytics, nitric oxide (in the form of its stable metabolite, nitrite anion). We calculated the activity of the enzyme NO-synthetase (NOS), which generates endogenous nitrite anion. These values characterize the protective effect of exogenous nucleic acids against the damaging influence of nitrite anion on erythrocytic membranes. Our focus on the changes in stability of erythrocytes in the process of autoimmune reactions is due to the large existing body of evidence supporting the immune-modulating properties of erythrocytes (Karalnik B. V., Erythrocytes, their receptors, and immunity, Uspekhi Sovremennoy Biologii., V.112, N.1, P52–61, 1992; Prokopenko L. H., Siplivaya L. E., Erythrocytes as modulators of immunologic reactions, Uspekhi Phiziologicheskikh Nauk., V.23, N.4, P.89–106, 1992), which has resulted in the use of the term "erythrocytal immune system".

Development of the autoimmune process was accompanied by a substantial decrease of acid resistance of erythrocytes during the early stage and, on the contrary, by a considerable excess over the norm during the final stage, in comparison with the resistance of normal erythrocytes.

Yeast RNA increased membrane stability, i.e., normalized the process of transportation of protons (which is attributed to the state of the protein and lipid components of etrythrocytal plasmatic membranes) during the initial stage and kept it stable, close to the norm, during the following stages of autoimmune reaction.

Further, it was demonstrated that, during the development of an autoimmune process, activities of NOS in rat blood changed. During the initial and final stages, an increased activation of NOS in rat blood was evidenced. Yeast RNA decreased NOS activity, so that at the final stage, the activity was practically normal.

Also, development of the autoimmune process was accompanied by a substantial decrease of acid resistance of erythrocytes during the early stage and, on the contrary, by a considerable excess over the norm during the final stage, in comparison with the resistance of normal erythrocytes. Yeast RNA increased membrane stability during the initial stage, by normalizing the process of proton transportation, which is dependent on the state of the protein and lipid components of etrythrocytal plasmatic membranes, and kept it stable, close to the norm, during the following stages of autoimmune reaction.

In view of the above, the protecting activities of yeast RNA as shown on the model of autoimmune process establish its ability to cure, not only allergic diseases, but other chronic inflammatory processes as well, such as arthritis, artherosclerosis, and other diseases that involve autoimmune reactions. ps 4. Model of Swelling Induced by Carrageenan in Rats To screen nucleic acid's anti-inflammatory action, we used a common model of inflammatory swelling of leg in mice provoked by a sub-plantar injection of carrageenan. Carrageenan-induced swelling is sensitive to the action of compounds which reduce capillary penetrability.

During the initial stage, a significant role in the mechanism of anti-inflammatory effect of carragenan is played by kinine, while at the later stage, proteolytic ferments and prostaglandins become more important. The carrageenan model has a slower development and is preserved for a sufficient time, which makes it possible to study the biochemical mechanism of the anti-inflammatory action of a drug. Therefore, we used this model to study the influence of yeast RNA on the synthesis of thromboxane and leukotriene. At the same time, we analyzed the influence of yeast RNA on NO-synthetase activity.

Analysis of the anti-inflammatory action of nucleic acids in the carrageenan model showed that they all have certain anti-inflammatory action. However, only yeast RNA in the concentration 10 mg of drug per mouse resulted in a 50% reduction of swelling. The concentrations of yeast RNA tested in mice represented 1 to 15 mg per mouse. Concentrations below 1 mg of yeast RNA preparation per mouse did not show any action. In concentrations above 15 mg, reduction of swelling was about 53–55%. Further, biochemical tests revealed a stabilizing influence of yeast RNA on the activity of NO-synthetase as well as on the quantities of thromboxane and leukotriene, which varied in the course of swelling process.

By contrast, aspirin, which was tested at the recommended therapeutic dose of 20 mg/kg, influenced swelling to a considerably smaller extend and did not show stabilizing properties at the level of biochemical metabolism.

5. Model of Acute Ischemia in Rats

Further analysis of yeast RNA was conducted on the model of acute ischemia-reperfusion of myocardium in rats. This model is based on a common fundamental mechanism in the development of a variety of different heart conditions, which includes alteration of structures and functions of the membranes in endotheliocytes, cardiocytes, and other heart cells. This alteration results in the degradation of membrane phospholipids and the creation of highly effective bio-active compounds, such as leukotrienes or thromboxanes, which have coronaroconstrictor, arythmogen, chemoactive, and pro-aggregant action (Bangham A. D., Hill M. W., Miller N., Preparation and use of liposom as model of biological membranes, Method in Membrane Biology, Acad.Press, V.1, N.Y, P.1–16, 1974).

As the tests demonstrated, yeast RNA, injected in rats intravenously in the concentration of 40 mg per rat, normalized heart function in acute infarcts. This was shown in a pronounced anti-arythmic action of the compound and a substantial decrease of the necrosis area in ischemized myocardium of heart. The drug almost completely normalized NO-synthetase activity in blood and in the border zone of ischemized heart. Yeast RNA injection normalized to a certain level the content of arachidonic acid in blood and heart of animals in acute infarctions. The injection of yeast RNA almost completely normalized the levels of eukosanoids in rat blood in ischemia cases. The activity of mieloperoxidase, the marker enzyme of neutrophils which helps to evaluate the preparation's anti-oxidant action, decreased almost twice in animals with infarct treated by yeast RNA.

The analysis of yeast RNA activity in the ischemia-reperfusion model in rats determined that the drug has a substantial stabilizing action in different cascades of inflammatory processes in the ischemized heart, which is expressed in its long-term anti-infarct action and a decreased size of the infarct area in myocardium.

On the basis of the study of yeast RNA action in ischemia-reperfusion of animal heart, we can conclude that yeast RNA has an anti-infarct action, or anti-inflammatory action in infarcts, through stabilization of the structure and function of membranes in endotheliocytes, cardiocytes, and other heart cells.

Experimental Procedures and Test Results

EXAMPLE 1
Method for Obtaining Yeast RNA

EXAMPLE 1.1
Production of Yeast RNA

From *Saccharomyces cerevisiae* was obtained RNA-D and from *Candida utilis* were obtained RNA-P, RNA-PN, and RNA-F. Yeast RNA extraction was conducted with a 10–12% solution of sodium chloride at 100–110° C. The RNA solution was separated from yeast sediment, cooled to 0° C. and acidified to pH 1–2 by hydrochloric acid. Deposited RNA was rinsed by ethyl alcohol, dried and dissolved in water. The solution was brought to pH 8.0–8.2 by sodium hydroxide. The solution with added pancreatin was kept at 37–40° C. for approximately 1 hour. The ferment was inactivated by boiling; afterwards, the solution was filtrated. RNA was sedimented by cooled ethyl alcohol, acidified by hydrochloric acid to pH 1–2, and dried. In this way, RNA-F was obtained. Further, the sediment was filtrated, rinsed in ethyl alcohol, and dissolved in water by adding sodium hydroxide to pH 6.2–6.5. RNA-PN was sedimented by alcohol. The sediment was filtrated and dried. RNA-P was educed from RNA-F by additional purification from protein by another pancreatin treatment and incubation for 1 hour at 37–40° C. Then, the ferment was inactivated by boiling for 5–10 min. The solution containing RNA-P was filtrated and sedimented by alcohol acidified to pH 1–2. The RNA-P sediment was filtrated, rinsed in ethyl alcohol and dried. The resulting compound has a grey-yellowish color.

TABLE 1

Chemical Analysis of Yeast RNA Preparations

| Type | RNA-P | RNA-D | RNA-F | RNA-PN |
| --- | --- | --- | --- | --- |
| Nitrogen content % | 15.49 | 15.16 | 14.16 | 14.65 |
| Phosphorus content % | 9.05 | 8.6 | 8.2 | 8.54 |
| Biuret reaction | (−) | (−) | (+) | (−) |
| DNA content % | 1 | 1.1 | 1.2 | 1.1 |

The tested RNA (RNA-P and RNA-D) had the following properties as shown in Table 1: N≧14.7%, P(total)≧8.6%, protein (biuret reaction)—negative, DNA (colometric)—2.0%, sugars (chromatography)—negative, polysaccharides (biological test)—negative.

EXAMPLE 1.2
Absence of Toxicity

We established that yeast RNA-P and RNA-D are non-toxic. Single or multiple doses of yeast RNA in bio-active amounts (250 to 500 mg per 1 kg of body weight), taken intra-abdominally, did not lead to substantial changes in the quantity of peripheral lymphocytes in mice. Such changes would be a characterizing indicator for endotoxins.

Analogous results were obtained for intravenous introduction of nucleic acids. We tested variations in the quantity of peripheral leukocytes in rabbits 1–3 hours after 100 mg yeast RNA-P or RNA-D solution was injected intravenously. Intravenously injected solution of 0.85% NaCl was used as the standard of non-toxicity. It was demonstrated that, analogously to the standard, an injection of yeast RNA-P or RNA-D does not cause a variation in the number of leukocytes within 3 hours of the introduction. In animals, which took 0.85% solution of NaCl, the quantity of leukocytes was equal to 13000±980, while those, who had RNA-P or RNA-D, showed accordingly 12700±850 and 12900±980, which is not abnormal. When the rabbits received injections of 10 mg of proteus polysaccharide, the quantity of leukocytes decreased in 1 hour from 13050±1100 to 2900±210, and remained at that level while the test lasted (3 hours). These results prove the non-toxicity of yeast RNA. Further, when 100 mg of yeast RNA-P or RNA-D per 1 kg of body weight was given to rabbits intravenously, no acute-phase C-reactive protein was determined, which indicates that there was no endotoxic action.

In addition, yeast RNA is not pyrogenic, which was shown on rabbits. Temperatures were taken 4 times a day, with 2-hour intervals, in a group of rabbits for 2 days. On the third day, the rabbits were injected with 0.85% of NaCl, and the temperatures were taken again 1, 2, and 3 hours after the injection. On the sixth day, the rats were divided into 3 groups, two of which received intravenously 100 mg of RNA-P and RNA-D, respectively. The temperatures were taken again. The control animals showed temperature fluctuations within 0.1° to 0.4° C. The tested animals had temperatures fluctuating within the same limits: 0.1° to 0.4° C. These results prove the non-pyrogenicity of yeast RNA.

EXAMPLE 2
Anti-Inflammatory Action of Nucleic Acids Based on the Model of Thrombocyte Aggregation in Vitro We studied the anti-inflammatory action of nucleic acids on the model of thrombocyte aggregation in vitro by the method of Born (Born L. V. R. The aggregation of blood platelets by diphosphate and its reversal, Nature, V.94, P.327, 1962). Venous human blood was taken in silicon tubes of Becton Dickson, which contained a 3.8% solution of sodium citrate. In order to receive thrombocytic-rich plasma, citrate blood was centrifuged at 1500 rev/min for 7 minutes. Plasma free of thrombocytes was obtained by centrifuging 2.0 ml of plasma taken from medium layers for 15 minutes at 3000 rev/min. We counted the number of thrombocytes in the thrombocytic-containing plasma, which was later diluted by the thrombocyte-free plasma to the final concentration $200.0-300.0\times10^8/l$.

An Aggregometer produced by "Tromlite" (Poland) was used for thrombocyte aggregation. In order to induce aggregation, arachidonic acid was diluted in Michaelis buffer in the proportion 1 mg/ml. Two tubes were inserted in the aggregometer, one of which contained 0.2 ml of thrombocyte-containing plasma, while the other one had 0.2 ml of thrombocyte-free plasma and 0.1 ml of isotonic solution of sodium chloride. After the device was switched on, 0.1 ml of arachidonic acid was added to the tube containing plasma with thrombocytes. Then, the light-transparency of thrombocyte-containing plasma was measured during 5 minutes, which indicated the stage of thrombocyte aggregation.

In a variation of the test for studying the influence of nucleic acids on thrombocyte aggregation, before measuring, the solution of thrombocyte plasma was preliminary incubated for 5 minutes at 37° C. with 0.1 ml of the nucleic acid at the corresponding concentration. 0.2 ml of isotonic solution of sodium chloride was added to the tube with thrombocyte-free plasma. After incubation, the device was switched off and 0.1 ml of arachidonic acid was added to the tube with thrombocytic plasma and a nucleic acid. In 5 minutes, measuring was done to determine the final stage of thrombocyte aggregation.

As the aggregation parameter, we used the index of aggregation of cells (IA), which is equal to:

$$IA = \frac{D1 - D2}{D1} \times 100\%$$

D1—optical density of thrombocyte-containing plasma with the induction of aggregation by the arachidonic acid.

D2—optical density of thrombocyte-containing plasma, which was preincubated with a nucleic acid and with an induction of aggregation by the arachidonic acid.

Statistical processing of the results was done by Student criteria and with the help of software as described in example 4.1.

The following nucleic acids, were studied: DNA-CT, DNA-EC, tRNA, and total yeast RNA-D in the final concentration $1 \times 10^{-2}\%$. Aspirin in the concentration 0.06 mg per tube, which contained thrombocytic plasma, was also tested as a standard anti-inflammatory agent.

The test results are shown on Table 2 below.

TABLE 2

Influence of Nucleic Acids and Aspirin on the Aggregation of Thrombocytes Induced by Arachidonic Acid

|  | RNA-D | Aspirin | DNA-CT | DNA-EC | t-RNA |
|---|---|---|---|---|---|
| M | 59,73 | 38,66 | 54,45 | 36,93 | 52,23 |
| +-m | 4,24 | 6,71 | 3,76 | 1,88 | 8,13 |
|  |  | P < 0.02 | P < 0.2 | P < 0.01 | P > 0.5 |

The test results showed that nucleic acids in the concentration $1 \times 10^{-2}\%$ inhibit aggregation of thrombocytes induced by arachidonic acid. Further, Yeast RNA-D in the concentration $1 \times 10^{-2}\%$ inhibited aggregation of the induced thrombocytes almost twice as effectively as aspirin (38.66%): yeast RNA-D showed 59.73% and transport E. coli RNA had 52.23%. DNA from chicken erythrocytes acted at the same level as aspirin (36.93%), while DNA from cattle thymus inhibited aggregation of thrombocytes by 54.45%, which is almost at the level of yeast RNA. Since DNA always contain a significant amount of RNA, it is probable that the inhibiting effect of DNA can be attributed to the RNA contained in DNA.

Further, an analysis of the influence of different concentrations of yeast RNA on the aggregation of induced thrombocytes showed that yeast RNA was effective in a wide range of concentrations from 0.1% to $1 \times 10^{-5}\%$ and inhibited aggregation by 78.5% and 14.2%, as shown in Table 3 below.

TABLE 3

Concentration-Dependence of the Influence of Yeast RNA-D on the Aggregation of Thrombocytes Induced by Arachidonic Acid

|  | RNA 0,1% | RNA $1 \times 10^{-2}\%$ | RNA $1 \times 10^{-3}\%$ | RNA $1 \times 10^{-4}\%$ | RNA $1 \times 10^{-5}\%$ |
|---|---|---|---|---|---|
| M | 78,58 | 53,08 | 28,88 | 43,35 | 14,23 |
| +-m | 7,51 | 3,23 | 1,63 | 10,3 | 4,98 |
|  |  | P < 0.01 | P < 0.001 | P < 0.01 | P > 0.001 |

Still further, it was demonstrated that the inhibiting effect on aggregation depends on the purity of yeast RNA and its sodium salt, as shown on Table 4 below.

TABLE 4

Influence of Yeast RNA-P, -PN and -F on the Aggregation of Thrombocytes Induced by Arachidonic Acid

| Conc. 0.1% | RNA-P | RNA-PN | RNA-F |
|---|---|---|---|
| M | 84,09 | 45,96 | 57,9 |
| +-m | 3,77 | 8,96 | 9,58 |
|  |  | P < 0.001 | P < 0.02 |
| Conc. $1 \times 10^{-2}\%$ | RNA-P | RNA-PN | RNA-F |
| M | 71.91 | 55.44 | 60.90 |
| +-m | 8,45 | 8,04 | 10,39 |
|  |  | P < 0.2 | P > 0.5 |
| Conc. $1 \times 10^{-3}\%$ | RNA-P | RNA-PN | RNA-F |
| M | 29,76 | 3,72 | 18,26 |
| +-m | 5,36 | 2,4 | 5,46 |
|  |  | P < 0.001 | P < 0.1 |

Table 4 shows that RNA-F containing protein admixtures and lower levels of nitrogen and phosphorus content acted less effectively in the range of concentrations from $1 \times 10^{-1}\%$ to $1 \times 10^{-3}\%$. For example, at its highest concentration, RNA-F inhibited thrombocytic aggregation by 57%, whereas at its lowest concentration, inhibition was only 22.7%. At the same time, well-purified RNA-P inhibited thrombocytic aggregation by a third more effectively, accordingly, by 84% and 29.7%. Also, when RNA was transformed into its sodium salt, the anti-aggregate properties decreased dramatically. Thus, RNA-PN, at its highest concentrations, was only half as effective (44.4%) as the acid form, while at its lowest concentration, RNA-PN did not show any anti-aggregate properties.

Therefore, based on the model of aggregation of thrombocytes induced by arachidonic acid, it was demonstrated that RNA compounds and, especially, purified yeast RNA, have pronounced anti-aggregate properties in a wide range of concentrations, which indicates their anti-inflammatory action.

EXAMPLE 3

Anti-Inflammatory Action of Nucleic Acid Based on the Model of Erythrocyte Membrane Stabilization in Vitro The membrane-stabilizing and anti-radical actions of nucleic acids were evaluated in rat erythrocytes in tests in vitro. Erythrocytal membranes were damaged by nitrite anion, a stable metabolite of nitric oxide, which causes oxide injuries in the protein (especially, hemoglobin) and lipid components of the membrane.

In order to evaluate the membrane-stabilizing action of nucleic acids against the influence of free radicals, we calculated the acid resistance of normal rat erythrocytes separated from blood plasma. Rat erythrocytes were rinsed thrice in the cold (4° C.) solution of 0.15M of NaCl. The layers of leukocytes and thrombocytes were removed. Acid lysis of the remaining erythrocytes was induced by adding 10 μl of the suspension, which was diluted to the concentration of erythrocytes ($0.7 \times 10^6$ cells per 1 ml of iso-osmotic medium), and which contained 0.14M of NaCl, 0.01M of the citrate-phosphate buffer pH=2.5, different doses (10 or 100 μg) of nucleic acids, and a stable concentration of nitric sodium, 250 μg per 1 ml, to initiate the oxide damage of erythrocytes.

Erythrocytal lysis was initiated by adding 1 ml 0.004N HCl; changes in existence were recorded at 750 nmol. The method of calculation is explained in Example 6.3. It was demonstrated that yeast RNA-D in the doses of 10 and 100 μg increased the level of total resistance of the erythrocytes from 288 units (control value recorded for the influence of NaNO$_2$ without yeast RNA) to 449 units (yeast RNA concentration 10 μg) and 437 units (yeast RNA concentration 100 μg), which is close to norm (475 units). RNA-PN increased total resistance to 328 units in the dose of 10 μg and to 415 units in the dose of 100 μg. RNA-P increased total resistance to 315 units in the dose of 10 μg and to 462 units in the dose of 100 μg (maximally close to the normal level of this indicator). RNA-F increased total resistance to 338 units in the dose of 10 μg and, on the contrary, somewhat decreased (to 271 units) in the dose of 100 μg.

DNA-CT increased total resistance to 338 units in the dose of 10 μg and to 654 units in the dose of 50 μg (which is double the control value and even greater than norm (without harmful influence of NaNO$_2$)). In the dose of 100 μg, however, its effect was the opposite—membrane-stabilizing, which was shown by a decreased total resistance to 158 units, which is almost half the control value.

DNA-EC in the dose of 100 μg did not change acid resistance of erythrocytes in our oxide-damage model. In the dose of 10 μg, it increased acid resistance to 408 units, which is a little lower than the calculated protector action of RNA-D (449 units in the dose of 10 μg).

Therefore, exogenous DNA, regardless of their origin, have significant anti-stabilizing influence on cellular membranes. Since they damage cellular membranes, they cannot be used as drugs or food supplements.

The preparation of t-RNA in both doses (10 μg to 279 units and 100 μg to 296 units μg) did not influence the acid resistance of erythrocytes.

The tests show that yeast RNA, when tested in vitro, shows membrane-stabilizing and anti-radical properties which depend on its form, origin, and purity. Well-purified yeast RNA-P, whose anti-inflammatory properties were studied more in detail, showed the best effectiveness.

EXAMPLE 4
Anti-Inflammatory Action of Nucleic Acid Based on the Model of Local Inflammation Provoked by Carrageenan (LPS)

was taken as control. 4 hours later after the carrageenan injection, the mice were killed via decapitation, and their back legs were detached from the bodies on the same level, a little higher the ankles. After that, the legs were carefully weighted, with 1 mg accuracy. Obtained results were statistically processed by the MultiFac 2.2. SPSS 8/0 software. The anti-inflammatory effect of the drug was calculated by the formula:

$$\text{Percentage of reduction of inflammation} = \frac{V_k - V_o}{V_k} \times 100\%$$

$V_k$—average increase of volume (mass) of the swollen leg in control mice $V_o$—average increase of volume (mass) of the swollen leg in treated mice In the first test, mice were divided into 8 groups. The first group consisted of control animals, which were injected intra-abdominally with 2 ml of PS. Also, 40 ml of PS was injected in the left leg. This group was studied to determine the influence of injection on the course of inflammation in a leg. The second group, control with LPS, took 2 mg of PS intra-abdominally and received LPS injections in the left leg. The third group took 2 mg of aspirin dissolved in PS in the concentration 0.4 mg per mouse. In the fourth, fifth and sixth groups, yeast RNA-D was dissolved in PS in respective concentrations 5, 10, and 15 mg in 2 ml of PS per animal. LPS was injected in the left leg to provoke swelling. The seventh and eighth groups were treated respectively by DNA-TC and DNA-EC, which were injected in the concentration 15 mg per mouse, as explained above for RNA-treated groups.

The right legs were left intact. 4 hours later, the animals were decapitated. Both legs were detached from the bodies and their masses were studied in each group of animals. Results of these tests on the anti-inflammatory action of nucleic acids are presented in Table 5 below.

TABLE 5

Influence of Nucleic Acids on Local Inflamation of Mice Legs

| Control + PS | Control + LPS | Aspirin | RNA-D 5 mg/m | RNA-D 10 mg/m | RNA-D 15 mg/m | DNA-TC 15 mg/m | DNA-EC 15 mg/m |
|---|---|---|---|---|---|---|---|
| 0 % of inhibition | 43.31 + 2.43 | 35.5 + 2.8 18.03% $P < 0.001$ | 27.4 + 2.05 36.74% $P < 0.001$ | 28.88 + 2.27 47.17% $P < 0.001$ | 20.3 + 3.17 53.13% $P < 0.001$ | 31.8 + 2.59 26.58% $P < 0.001$ | 289 33.27% $P < 0.001$ |

EXAMPLE 4.1
Action of Yeast RNA on Swelling in the Model of Local Inflammation Provoked by Carrageenan (PS) in Vivo To study the anti-inflammatory action of drugs, we used the model of local inflammation in mice. Inflammation in BALB-line mice was modeled with the help of carrageenan, a classical phlogogenic agent. 30 minutes before the injection, the mice were injected intra-abdominally with drug, which was dissolved in 2 mg of physiological solution (PS). Carrageenan (LPS) produced by Serva Fein Biochemica (Germany) was prepared in the form of a 1% solution in PS. The obtained viscous solution, 40 mcl, was injected subplantally in the left back leg. The right, intact leg As shown in Table 5, aspirin in the administered concentration reduced the development of swelling in mouse legs by 18.03%. This is consistent with the results cited in other papers for this model and proves the adequacy of the modeled inflammation. Aspirin concentrations also correspond to the dose of 20 mg/kg which is currently recommended for a clinical use and which has fewer negative consequences for a long-term use in various forms of inflammatory processes.

Further, the preparation of yeast RNA-D showed a significant anti-inflammatory action, which directly depended on the concentration. In the concentrations 5, 10, and 15 mg per mouse, the drug inhibited swelling by 36.74%, 47.17%, and 53.13% accordingly. The preparation of DNA-TC and DNA-EC also showed some anti-inflammatory action, though in quite high concentrations (15 mg per mouse), and indicators of the anti-inflammatory action were twice as low (26.58% and 33.27%, respectively).

On the basis of the results, we can conclude that nucleic acids have considerably improved anti-inflammatory properties as compared to aspirin, and yeast RNA has by far the most significant action.

EXAMPLE 4.2

Action of Yeast RNA on Biochemical Indicia in the Model of Local Inflammation Provoked by Carrageenan (LPS) in Vitro The anti-inflammatory action of yeast RNA was compared with the action of aspirin in the dynamics of a developing inflammatory reaction ($0^{th}$, $30^{th}$, $60^{th}$, $320^{th}$ min) on mice after LPS injection. We tested the influence of yeast RNA on the activity of NO-synthetase ferment (NOS) in blood plasma and in erythrocytes, as well as on the content in blood plasma of free arachidonic acid and products of its oxide metabolism, carried out in lypoxygenase (leukotriene C4 ($LTC_4$)) and cyclooxygenase (thromboxane $B_2$ ($TxB_2$)) ways.

EXAMPLE 4.2.1

Action of Yeast RNA on the Activity of NO-Synthetase

The activity in blood plasma and erythrocytes of the enzyme NO-synthetase was measured by colometric method applied to the outcome of reaction, nitrite anion. (Yan L., Vandivier R. W., Suffredini A. F., Danner R. L., Human polymorphonuclear leukocytes lack detectable nitric oxide synthetase activity. J.Immunol., 15; 153(4): 1825–1834; 1994) The incubation mix (1 ml) consisted of 50 mM of HEPES (pH=7,4), 1,25 mM of $CaCl_2$, 1 mM of NADPH, 80 mcM FAD, 20 mcM of tetrahydrobiopterine, 13 mcg/ml of calmoduline 1 mM of L-arginine, 60 mM of L-valine, 100 units/ml of superoxyddismutase. HEPES is N(2 hydroxyetyl)-1-piperazineethanesulfonic acid by Sigma Chemical Co. (USA), NADPH is beta-nicotinamide adenine di-nucleotide phosphate in reduced form by Sigma Chemical Co. (USA). The reaction was initiated by adding 0.1 ml of a probe containing 500 microgram of general protein determined by Bredford method. Incubation at 27° C. lasted for 60 minutes. The reaction was terminated by adding 0.2 ml of 2N $HClO_4$. The mix was centrifuged at 10000 g for 10 minutes, and the supernatant liquid was used to determine the content of nitrite-anion (stable metabolite of nitrogen oxide).

Nitrite anion was determined using the reagent of Gris in colometric reaction as described in Green et al. (Green L. C., Waagner D. A., Glogowski J. et al., Analysis of nitrate, nitrite and [15N] nitrate in biological fluids, Anal.Biochem., 126(1): 131–138;1982). The Gris reagent was prepared by mixing equal parts of 0.1% water solution of naphthylene-diaminehydrochloride and 1% solution of sulfanilamide in 5% $H_3PO_4$ immediately before the measurement. The measurement was carried out in non-protein aliquots of probe by adding Gris reagent in the 1:1 proportion. In 5 minutes after mixing, the extinction at 543 hm was measured. The quantity of $NO_2^-$ was measured by standard curve built for $NaNO_2$. The test results are presented in Table 6 below.

TABLE 6

Action of Yeast RNA and Aspirin on the Activity of NOS in Mouse Blood Plasma after Carrageenan Injection (in picomol per 1 min per 1 mg of protein; M ± m; n = 5)

| | LPS (Control) | | | | + Yeast RNA | | | + Aspirin |
|---|---|---|---|---|---|---|---|---|
| | 0 min (norm) | 30 min | 60 min | 320 min | 30 min | 60 min | 320 min | 320 min |
| M ± | 18.41 | 189.45 | 72.03 | 110.48 | 35.40 | 9.61 | 107.14 | 42.24 |
| m | 2.24 | 21.34 | 9.25 | 22.79 | 7.73 | 0.96 | 13.26 | 4.50 |
| P1 | | <0.001 | <0.001 | <0.01 | >0.05 | <0.01 | <0.001 | <0.01 |
| P2 | | | | | <0.01 | <0.01 | >0.5 | >0.05 |

P1—certainty of difference with respect to the norm (before LPS injection)
P2—certainty of difference with respect to the control (without yeast RNA)

Table 6 shows that, without prior injection of yeast RNA control case, a dramatic increase (more than tenfold) of NOS activity in blood plasma was evidenced for 30 minutes after LPS was injected. Then, enzymatic activity decreased with a later minor increase (though at a level much higher than normal).

A prior injection of yeast RNA in mice significantly decreased the rise of NOS activity in blood plasma during the initial stage (30 to 60 minutes) of inflammatory development. This protector property of yeast RNA was not evident on the $320^{th}$ minute of inflammatory development, while an aspirin injection reduced NOS activity exactly during this period of time.

Hence, yeast RNA has a pronounced inhibiting action on activation of the oxide way of L-arginine metabolism after the introduction of LPS, which is expressed by inhibiting the activity of NOS in blood plasma.

Since various isoforms of NOS, both constitutive and inducible, are present in different nucleus cells of blood plasma: neutrophyles, thrombocytes, lymphocytes, and macrophages (Hibbs J. B., Taintor R. R., Vavrin Z., Rachlin E. M., Nitric oxide: a cytotoxic activated macrophage effector molecule. Biochem. Biophis. Res. Commun. 30; 157(1); 87–94; 1988; Salkowski C. A., Regulation of inducible nitric oxid messenger RNA-expression and nitric oxid production by lipopolysaccharide in vivo: the role of macrophage, endogenous IFN-gamma and TNF receptor-1-mediated signaling. J.Immunol. 15; 158(2): 905–912; 1997) we may infer that in the initial stage after LPS introduction ($30^{th}$–$60^{th}$ minute), an activation of the constitutive forms (neuronal and endothelial) takes place, while the inducible form (iNOS) of blood macrophages is probably activated in the later period ($320^{th}$ minute).

Further, Table 7 below shows the dynamics of changing NOS activity in mice blood erythrocytes after LPS introduction. Control animals showed a minor increase of NOS activity on the $30^{th}$ minute, which was replaced by a significant (almost double) decrease of NOS activity in erythrocytes.

discussed in Tsunamoto et al. (Tsunamoto K., Todo S., Imashuku S. Separation of prostaglandines and thromboxane by two-dimensional thin-layer chromatography. J.Chromatog. 3; 417(2); 414–419; 1987. The content of stable metabolite of thromboxane A2 ($TXB_2$) was studied in probes by radio-immune method with $TXB_2$ [$^3$H] RIA Kit,

TABLE 7

Action of Yeast RNA and Aspirin on the Activity
of NOS in Mouse Erythrocytes after Carrageenan Injection
(in picomol per 1 min per 1 mg of protein; M ± m; n = 5)

|  | LPS (Control) | | | | + Yeast RNA | | | + Aspirin |
| --- | --- | --- | --- | --- | --- | --- | --- | --- |
|  | 0 min | | | | | | | |
|  | (norm) | 30 min | 60 min | 320 min | 30 min | 60 min | 320 min | 320 min |
| M ± | 4.336 | 7.768 | 2.323 | 2.232 | 14.245 | 10.213 | 1.146 | 3.613 |
| m | 1.105 | 0.999 | 0.383 | 0.515 | 1.109 | 1.924 | 0.242 | 0.595 |
| P1 |  | >0.05 | >0.1 | >0.1 | <0.001 | <0.05 | <0.05 | >0.5 |
| P2 |  |  |  |  | <0.01 | <0.01 | >0.05 | <0.2 |

P1—certainty of difference with respect to the norm (before carrageenan injection)
P2—certainty of difference with respect to the control (without yeast RNA)

The same dynamics of modification in NOS activity, or even a more pronounced one, was evidenced in mice erythrocytes after a prior injection of yeast RNA. Thus, an increase of NOS activity (respectively more than three-fold and two-fold) was manifested on the $30^{th}$ and $60^{th}$ minute. A reliable (more than three-fold) decrease of NOS activity in erythrocytes was recorded on the $320^{th}$ minute of LPS action.

Some authors (Chen L. Y., Mehta J. L., Evidence for the presence of L-arginine-nitric oxide pathway in human red blood cells: relevance in the effects of red blood cells on plateled function, J. Cardiovasc. Pharmacol. 32(1): 57–61; 1998) indicate that erythrocytes contain a constitutive, Ca-dependent isoform of NOS. Thus, it is possible that the increased activity of erythrocytal NOS during the initial stage of inflammatory reaction, which was induced by LPS introduction, is caused by increased levels of intercellular calcium in the red cells of blood plasma.

by Amersham International PLC (England) (McCann D. S., Tokarsky J., Sorkin R. P., Radioimmuno assay for plasma thromboxane B2. Clin.Chem., 27(8): 1417–1420, 1981). The content of $LTC_4$ was tested in probes by radio-immune method with $LTC_4$ [$^3$H] RIA Kit by Du Pont Ltd. Hertfordshire, (UK) (Levine L., Morgan R. A., Levis R. A. et al., Radioimmunoassay of the leukotrienes of slow reactivity substance of anaphylaxis. Proc. Natl. Acad. Sci. USA. 78(12): 7692–7696; 1981).

Table 8 below demonstrates the dynamics of changes of free arachidonic acid in mice blood plasma after LPS introduction.

TABLE 8

Action of Yeast RNA and Aspirin on the Content of Free
Arachidonic Acid in Mouse Blood Plasma after Carrageenan Injection
(in nanomol per 1 mg of protein; M ± m; n = 5)

|  | LPS (Control) | | | | + Yeast RNA | | | + Aspirin |
| --- | --- | --- | --- | --- | --- | --- | --- | --- |
|  | 0 min | | | | | | | |
|  | (norm) | 30 min | 60 min | 320 min | 30 min | 60 min | 320 min | 320 min |
| M ± | 2.54 | 2.36 | 3.34 | 3.37 | 1.97 | 1.60 | 2.66 | 2.64 |
| m | 0.26 | 0.23 | 0.37 | 0.11 | 0.13 | 0.16 | 0.20 | 0.13 |
| P1 |  | <0.1 | >0.1 | <0.05 | >0.05 | >0.02 | >0.1 | >0.1 |
| P2 |  |  |  |  | <0.01 | <0.01 | <0.02 | <0.01 |

P1—certainty of difference with respect to the norm (before carrageenan injection)
P2—certainty of difference with respect to the control (without yeast RNA)

EXAMPLE 4.2.2
Action of Yeast RNA on Oxidizing Metabolism of Arachidonic Acid

The content of free arachidonic acid (AA) was measured by two-dimensional thin-layer chromatography (TLC) as As shown in Table 8, the control animals demonstrated increased levels of arachidonic acid only on the $320^{th}$ minute after LPS introduction. Yeast RNA evidently decreased AA content in blood plasma on the $60^{th}$ minute of LPS action. A decrease on the $30^{th}$ minute was not evident. On the $320^{th}$ minute after LPS introduction yeast RNA evidently decesased the content of AA in blood plasma in comparison with the control group.

It is known that free arachidonic acid is produced when membrane phospholipids are hydrolyzed with AA phospholipase, which is activated at increased levels of free ionized calcium (Leslie C. C., Channon J. Y., Anionic phospholipids stimulate an arachinoil-hydrolyzining phospholipase A2 from macrophage and reduce the calcium requirement for activity. Biochim. Biophys. Acta. 6; 1045 (3), 261–270; 1990) Besides, there are other possible ways of releasing free AA, for example, hydrolysis of cholesterol ethers by cholesterolesterase (Moscat J., Moreno F. Herrero C.,et al., Arachidonic acid releasing systems in pig aorta endothelial cells, Biochem.Biophys Res.Commun. 30; 139 (3): 1098–1103; 1986). Since, the first way of synthesis of free arachidonic acid is more frequent in inflammatory processes, the test results indicate that yeast RNA possibly inhibits the activity of phospholipase in blood plasma.

Further, Table 9 below shows the action of yeast RNA on the contents of thromboxane $B_2$, a stable metabolite of $A_2$ thromboxane which is produced during oxidizing cyclooxygenase metabolism of arachidonic acid.

TABLE 9

Action of Yeast RNA and Aspirin on the Content of Thromboxane in Mouse Blood Plasma after Carrageenan Injection
(in picomol per 1 mg of protein; M ± m; n = 5)

|  | LPS (Control) | | | | + Yeast RNA | | | + Aspirin |
| --- | --- | --- | --- | --- | --- | --- | --- | --- |
|  | 0 min (norm) | 30 min | 60 min | 320 min | 30 min | 60 min | 320 min | 320 min |
| M ± | 142.610 | 415.250 | 578.775 | 358.240 | 394.940 | 560.813 | 217.602 | 153.903 |
| m | 34.210 | 66.600 | 123.800 | 11.150 | 23.550 | 67.280 | 32.270 | 15.880 |
| P1 |  | <0.1 | <0.2 | <0.001 | <0.001 | <0.001 | <0.2 | >0.5 |
| P2 |  |  |  |  | >0.5 | >0.5 | <0.001 | <0.001 |

P1—certainty of difference with respect to the norm (before carrageenan injection)
P2—certainty of difference with respect to the control (without yeast RNA)

As shown in Table 9, after LPS introduction, a dramatic increase of $TXB_2$ pools in mice plasma was evidenced on the $30^{th}$ and, especially, on the $60^{th}$ minute. On the $320^{th}$ minute, the levels of $TXB_2$ started to drop. Yeast RNA, like aspirin, which is a known inhibitor of the cyclooxygenase metabolism of arachidonic acid (cyclooxygenase and thromboxanesynthetase), intensifies such a decrease of $TXB_2$ levels after their rapid increase in the early stage of inflammatory processes.

Next, Table 10 shows the dynamics of changes in the contents of peptidoleukotriene C4, a metabolite of lypoxygenase oxidation of AA, in mice blood plasma after LPS injection.

As shown in Table 10, the control group of animals showed an increase of $LTC_4$ contents in the interval between $30^{th}$ and $60^{th}$ minute, with a slight decrease against the normal level on the $320^{th}$ minute. Animals taking yeast RNA showed $LTC_4$ levels, which were lower than control on the $30^{th}$ and $320^{th}$ minutes of LPS action. Aspirin showed a similar inhibiting action, which was more pronounced than the action of yeast RNA on the $320^{th}$ minute.

In conclusion, the test results above indicate that yeast RNA, not only inhibits the generation of free arachidonic acid after LPS introduction, but also inhibits its oxidation, both through lypoxygenase and cyclooxygenase.

EXAMPLE 5

Anti-Inflammatory Action of Yeast RNA Based on the Model of Ischemia-Reperfusion in Rats

EXAMPLE 5.1

Cardioprotective Action of Yeast RNA 13 white rats with body mass 200–250 g were anesthetized with urethane and received intra-abdominal injections at 1.25 g/kg (Kogan A. H., Modeling the myocardial infarction, M., 1979). A tracheostome with inserted intubation pipe was placed on the rats. Artificial ventilation of lungs was provided by Vita-1 device. Skin and other tissues down to the intercostal muscles were incised with a 2–3 mm indention from the middle sternal line. The 4–4.5 cm. incision stretched from the jugular undercut to the sword-

TABLE 10

Action of Yeast RNA and Aspirin on the Content of Leukotriene C4 in Mouse Blood Plasma after Carrageenan Injection
(in picomol per 1 mg of protein; M ± m; n = 5)

|  | LPS (Control) | | | | + Yeast RNA | | | + Aspirin |
| --- | --- | --- | --- | --- | --- | --- | --- | --- |
|  | 0 min (norm) | 30 min | 60 min | 320 min | 30 min | 60 min | 320 min | 320 min |
| M ± | 71.60 | 156.64 | 266.33 | 226.78 | 92.18 | 227.00 | 129.35 | 93.99 |
| m | 10.72 | 10.03 | 41.09 | 7.48 | 15.66 | 36.12 | 19.25 | 1.99 |
| P1 |  | <0.001 | <0.01 | <0.001 | <0.5 | <0.01 | <0.5 | <0.1 |
| P2 |  |  |  |  | <0.02 | <0.5 | <0.01 | <0.001 |

P1—certainty of difference with respect to the norm (before carrageenan injection)
P2—certainty of difference with respect to the control (without yeast RNA)

shaped appendix. The lower parts of the $2^{nd}$, $3^{rd}$, and $4^{th}$ ribs, as well as the intercostal muscle between the $3^{rd}$ and the $4^{th}$ ribs, were dissected by eye scissors. The initial section of the left coronary artery is usually located in the space between left auricle's eye and pulmonary cone.

A strip of myocardium sized 1.5–2 mm×1–1.5 mm was stitched up with a 3/0 atraumatic needle, while going along the initial section of the artery, which could easily be seen. The revealed ligature was bandaged around the artery and surrounding muscles. Then we started the observation of the initial macro-signs of ischemia and developing infarction. During the first 10–20 seconds of ischemia, the tissue turned pale, especially in the upper portion of heart, and later changed partially or totally to blue (cyanosis). Contractions of the occlusion zone weakened, and it dilated. ECG's at the same standard distance from the extremities had been continuously recorded during the 30 minutes of ischemia and 60 minutes of reperfusion. 200 mg/kg of yeast RNA and 20 mg/kg of aspirin were injected 30 minutes before the start of ischemia.

To determine the area and size of the post-infarction scar in rats, sections of myocardium were dyed in accordance with the p-nitrobluetetrazolium method (Mueller B., Maass B., Krause W., Witt W., Limitation of myocardial unperfused area and necrotic zone 24 hours and 7 days after coronary artery ligation in rats by the stable prostacyclin analogue iloprost, Prostaglandins Leucot. Med. 21(3): 331–340; 1986). After reperfusion, the animals were heparinized (150 IU/kg i.v.) the hearts removed in deep ether aesthesia and retrogradely perfused with a solution of 0.05% p-nitroblutetrazolium in phosphate buffer (30 min;100 mmHg;37 C.). After 24 hours fixation in formaldehyde solution the ventricles were weighed, transversely sectioned into 5 slices each, and an unstained area was divided from the stained myocardium and weighed. The necrotic zone was calculated.

Analysis of the necrosis zone 60 minutes after ischemia determined that the risk zone in the left ventricle of the heart constituted 33.3+3.4% of the left ventricle mass. In the control group, the infarction zone constituted 60.3+3.8% of the risk zone. Yeast RNA injection 30 minutes before the start of infarction on 41% decreased the proportion between infarction and risk zones to 32.1%.

Analysis of ECG in ischemia-reperfussion of myocardium in rats showed that a prior injection of yeast RNA compound decreased the amount of extasystols. In only one of the five rats in this group, 4 extrasystols were detected. In the control group, which consisted of rats not treated by yeast RNA, we registered extrasystols in 3 rats, on average 8.7+1.7. The intervals of paroxysmal tachycardia in the control group lasted longer: 2 out of five rats had the episodes lasting for 4.2+1.3 sec on average.

In the group treated by yeast RNA only one rat out of five had an interval of paroxysmal tachycardia, which lasted for 1.5 sec. ECG analysis showed that yeast RNA improves the heart function in ischemia-reperfussion of myocardium, stabilizes the leading heart system, and has a significant anti-arrhythmic action by decreasing the quantity of extrasystols and shortening the paroxysmal tachycardia interval.

In conclusion, these test results show that yeast RNA has a pronounced cardio-protector action in infarction of myocardium in rats.

EXAMPLE 5.2
Action of Yeast RNA on the Activity of Myeloperoxydase in the Ischemiazed Part of Myocardium The mieloperoxydase activity (MPA) was studied in myocardium using the method of Bradley et al. (Bradley P. P., Priebet D. A., Christensen R. D. et al., Measurement of cutateous inflammation: estimation of neutrophil content with an enzyme marker, J. Invest. Dermatol., 78(3): 206–209; 1982) in the modification by Grisfwold et al. (Griswold D. E., Hillegass L. M., Hill D. E. et al., Method for quantification of myocardial infarction and inflammatory cell infiltration in rat cardial tissue, J. Pharmacol. Methods, 20(3): 225–235, 1988). For this purpose, the heart was extracted and rinsed in physiological solution, which was cooled to 0° C. After rinsing, a section of myocardium (1 g of the tissue) in the central zone of ischeria was cut out and frozen to −30° C. The final fraction was prepared as a 10% haemogenate with extractive buffer containing 0.5% hexadecyltrimethyl ammonium bromide (pH 6.0) at room temperature. Afterwards, it was centrifuged for 20 minutes at 4° C. and 12000 g.

The upper fraction (30 microliters) was used for a reaction with 0.167 mg/ml of O-dianisodine in 50 millimole/l of potassium phosphate buffer (pH 6.0). The reaction was launched with adding 0.005% solution of $H_2O_2$. The reaction had been continuously tested for 5 minutes at 460 hm wave length, and with readings taken every minute. A chart indicating the readings was prepared. A unit of MPA was defined as the quantity of ferment, which destroys 1 micromole/min $H_2O_2$ at 25° C. The data was calculated as MPA per 1 gram of tissue.

Ischemia and reperfusion provoked an acute inflammatory response, the central role of which is believed to be played by neutrophils (Entman M. L., Smith C. W., Postreperfusion inflammation: a model for reaction to injury in cardiovascular disease, Cardiovasc. Res. 28(9): 1301–1311, 1994). Because the reperfusion of ischemiazed myocardium is accompanied by intensive concentration of neutrophils within the risk zone (Hearse D. J., Bolli R., Reperfusion induced injury: manifestation, mechanisms and clinical relevance. Cardiovasc. Res. 26(2): 101–108; 1992), Which releases various inflammatory mediators, such as free oxygen radicals, cytokines, and haemokines, and increases ischemic-perfusion damages of myocardium (Entman M. L., Micheal L., Rossen R. D., et al. Inflammation in the course of early myocardial ischemia, FASEB J., 5(11): 2529–2537; 1991), and a direct link exists between the intensity of concentration of neutrophilis in ischemiazed myocardium and the activity of mieloperoxydase, a special ferment contained in neutrophils, so that an increase of MPA activity directly correlates with the quantity of leukocytes migrating to the inflammation zone.

Analysis of the activity of myeloperoxydase in the ischemized sector of myocardium after 30 minutes of occlusion and 1 hour of reperfusion of the left coronary artery in rats, showed that it is equal to 211.8+16.7 units per 1 g of tissue in the control group. When the animals were injected with aspirin, the activity decreased to 176.1+5.9. RNA-D injection decreased the activity by one third to 152.3+9.8 units per 1 g of tissue.

Further, an intravenous dose of 200 microgram/kg of yeast RNA in rats, injected 30 minutes before ischemia, decreased the concentration of neutrophils in the risk zone after an hour-long reperfuision. The quantity of neutrophils decreased approximately by 30% which is twice the result obtained for aspirin (20 microgram/kg). This allows us to conclude that the yeast RNA will be effective when used as a cardio-protector in cases of ischemia and myocardial reperfusion.

EXAMPLE 5.3
Action of Yeast RNA on the Activity of NOS in Ischemia Cases

The tests were conducted on rats with an infarct of myocardium experimentally induced by occlusion of the coronary artery for 30 minutes. Blood was taken from the coronary artery and from the heart, which was divided into the intact zone, border zone, and infarction zone. The activity of NOS ferment was measured in different heart zones and in blood. Also, we measured the contents of free arachidonic acid (heart and blood) and products of its oxidizing metabolism (blood). The test results are shown in Table 11 below.

TABLE 11

Action of Yeast RNA on the Activity of NOS in Rat Heart in Ischemia
(in picomol per 1 mg of protein; M ± m; n = 5)

| | | Ischemia 30 min (Control) | | | Ischemia 30 min + Yeast RNA | | |
|---|---|---|---|---|---|---|---|
| | Norm | Border zone | Infarction zone | Intact | Border zone | Infarction zone | Intact |
| M ± | 46.500 | 259.310 | 185.626 | 129.655 | 59.634 | 115.122 | 122.630 |
| m | 7.000 | 60.683 | 48.635 | 30.341 | 11.649 | 40.509 | 26.413 |
| P1 | | <0.01 | <0.05 | <0.2 | <0.5 | <0.1 | >0.05 |
| P2 | | | | | <0.2 | <0.5 | <0.05 |

P1—certainty of difference with respect to the norm (before ischemia)
P2—certainty of difference with respect to the control (without yeast RNA)

The data in Table 11 demonstrates that, during a short-term ischemia, the activity of NOS increased more than three-fold in the infarction zone (115±40 and 186±49 pmol/min on 1 mg of protein accordingly, in the test and control groups). Hence, yeast RNA almost completely normalized the activity of NOS in the border zone of ischemic heart infarction, which may be one of the mechanisms of its cardio-protecting action.

Since cardiomyocytes contain both the inducible NOS isoform and its constituent isoforms (Balligand J. L., Kobzik L., Han X., et al., Nitric oxide-dependent parasympathetic signaling is due to activation of constitutive endothelial (type III) nitric oxid synthetase in cardiac myocyte, J. Bio.Chem., 16; 270(24); 14582–14586; 1995; Peng H. B., Spiecker M., Liao J. K. Inducible nitric oxid: an autoregulatory feedback inhibitor of vascular inflammation, J.Immunol. 15; 161(4): 1970–1976; 1998; Oddis C. V., Simmons R. L., Haffler B. G., Finkel M. S. cAMP enchances inducible nitric oxid synthase mRNA stability in cardiac myocytes, Am. J. Physiol. 269(6): H2044–2050; 1995), taking into account the short period (30 minutes) of ischemia, it is inferred that yeast RNA inhibits the constituent isoform of NOS. At the same time, since iNOS is present, yeast RNA may also act as an inhibitor of activity of inducible NOS in ischemic cardiomyocytes.

Further, the influence of yeast RNA on NOS activity in rat blood in ischemia is shown in Table 12 below in Example 5.4. The test results in Table 12 show that, unlike in the heart, the activity of NOS in the blood of control animals in ischemia decreased twice (14.22+1.43 and 30.35+3.40 pmol per 1 mg of protein accordingly in ischemia and normoxia), which is usual for hypoxia (Arnet W. A., McMillan A., Dinerman J. L. et al., Regulation of endothelial nitric oxid synthase during hypoxia, J.Biol.Chem. 271(25): 15069–15073; 1996). Introduction of yeast RNA almost completely normalized NOS activity in rat blood after a 30-minute ischemia.

EXAMPLE 5.4

Action of Yeast RNA on the Oxidizing Metabolism of Arachidonic Acid in Ischemia Cases Table 12 below shows the content of NOS and free arachidonic acid in the blood of normal and ischemic animals.

TABLE 12

Action of Yeast RNA on the Activity of NOS and
Content of Arachidonic Acid in Rat Blood in Ischemia

| | NOS Activity in picomol per 1 mg protein; | | | Content of free Arachidonic acid (nmol/1 mg of protein) | | |
|---|---|---|---|---|---|---|
| | M ± m; n = 5 | | | Ischemia | | |
| | Norm | Ischemia 30 min | Ischemia + Yeast RNA | Norm | 30 min (control) | Ischemia + Yeast RNA |
| M ± | 30.35 | 14.22 | 26.45 | 0.77 | 0.24 | 0.48 |
| m | 3.40 | 1.43 | 3.73 | 0.13 | 0.04 | 0.02 |
| P1 | | <0.01 | <0.5 | | <0.01 | >0.05 |
| P2 | | | <0.05 | | | <0.01 |

P1—certainty of difference with respect to the norm (before ischemia)
P2—certainty of difference with respect to the control (without yeast RNA)

As shown in Table 12, the control group of animals demonstrated decreased levels of free AA more than three-fold (0.77±1.43 and 30.35±3.40 nmol/min on 1 mg of protein accordingly in normoxia and ischemia cases). The introduction of yeast RNA somewhat normalized the content of AA, by increasing it twice against the control value (P<0.001).

Table 13 indicates the content of free arachidonic acid in different heart zones in ischemia cases.

TABLE 13

Action of Yeast RNA on the Content of Free Arachidonic Acid in Rat Heart in Ischemia
(in nmol per 1 mg of protein; M − m; n = 5)

|  | Ischemia 30 min (Control) | | | Ischemia 30 min + Yeast RNA | | |
| --- | --- | --- | --- | --- | --- | --- |
|  | Norm | Border zone | Infarction zone | Intact | Border zone | Infarction zone | Intact |
| M ± | 4.827 | 9.910 | 9.716 | 9.813 | 7.270 | 8.530 | 7.900 |
| m | 0.378 | 1.003 | 0.947 | 0.919 | 0.456 | 0.741 | 0.493 |
| P1 |  | <0.01 | <0.01 | <0.001 | <0.01 | <0.01 | <0.01 |
| P2 |  |  |  |  | >0.05 | >0.05 | >0.5 |

P1—certainty of difference with respect to the norm (before ischemia)
P2—certainty of difference with respect to the control (without yeast RNA)

As shown in Table 13, the control group of animals demonstrated a reliable (more than two-fold, P<0.01) increase of AA levels both in the border and infarction zones of rat hearts. The introduction of yeast RNA somewhat decreased the level of arachidonic acid in both heart zones, but the difference was not evident (P>0.05).

Table 14 below shows the action of yeast RNA on the levels of eicosanoids in rat blood in ischemia cases.

TABLE 14

Action of Yeast RNA Compound on Eukosanoids in Rat Blood in
Ischemia (in picomol per 1 mg of protein; M-m; n = 5)

|  | Thromboxane B2 | | | Leucotriens C4 | | |
| --- | --- | --- | --- | --- | --- | --- |
|  | Norm | Ischemia 30 min (control) | Ischemia + Yeast RNA | Norm | Ischemia 30 min (control) | Ischemia + Yeast RNA |
| M | 53.00 | 130.72 | 62.49 | 24.10 | 39.62 | 25.69 |
| +−m | 10.67 | 33.92 | 7.98 | 3.94 | 10.18 | 4.04 |
| P1 |  | <0.05 | >0.5 |  | <0.2 | >0.5 |
| P2 |  |  | <0.1 |  |  | <0.5 |

P1 - certainty of difference with respect to the norm (before ischemia)
P2 - certainty of difference with respect to the control (without yeast RNA)

As shown in Table 14, the control group of animals demonstrated more increased levels of products of cyclooxygenase reaction of $TBX_2$ (more than two-fold, but the difference is not evident—P>0.05) rather than the levels of the product of lipoxygenase reaction $LTC_4$ (P<0.2). The introduction of yeast RNA almost completely normalized that content of eicosanoids in rat blood in ischemia cases.

In conclusion, in addition to the modulating influence on NOS activity in ischemia (inhibition in cardiomyocytes and, on the contrary, increase in blood), the cardio-protecting action of yeast RNA may also be mediated by modulating the oxidizing metabolism of arachidonic acid.

EXAMPLE 6
Anti-Inflammatory Action of Yeast RNA Based on the Model of Auto-Immune Pathology Model (Adjuvant Arthritis) in Vivo Adjuvant arthritis develops after rats are injected with Freud's adjuvant and is a part of the generalized process, which is accompanied by the impairment of bone and connecting tissues. Morphological tests show, that during the development of adjuvant arthritis, inflammatory-degenerative changes emerge in tissues surrounding the joint as well as inside the articular bursa and in joint cartilages. It is believed that this inflammatory reaction has all the properties of an immunologic process and constitutes a delayed immune reaction to a microbe antigen. The pathological process of adjuvant arthritis is very similar to arthritis in humans.

EXAMPLE 6.1
Action of Yeast RNA in an Auto-Immune Pathology Model (Adjuvant Arthrtis)

Adjuvant arthritis was modeled in rat males according to Courtright et al. (Courtright L. J., Kuzell W. C., Sparing effect of neurological deficit and trauma on the course of adjuvant arthritis in the rat, Ann. Reum. Dis. 24(4): 360–368; 1965). Control animals received a single hypodermic dose of 0.1 ml of standard Freud's adjuvant in the distal part of the tail. Adjuvant arthritis developed on the 14–20$^{th}$ day after the injection. Arthritis symptoms were determined by X-rays: a darkened area and shadows around the joints of back legs imply a starting impairment of the joint and gristle tissue.

In the test group yeast RNA was diluted in a 0.9% concentration of NaCl, was injected intra-abdominally in the concentration 100 mg per rat, a day before the injection of Freud's adjuvant. Yeast RNA has been also introduced after adjuvant's injection in three series within 4 days with three-day intervals.

Results of the analysis showed that arthritis in the control group started to develop on the 14$^{th}$ day and was manifested by exudative-proliferate growth of the synovial capsule and gristle impairment. On the 20$^{th}$ day, a hardening of tissue around the joint was witnessed and fibrosis of the synovial capsule started. On the 30$^{th}$ day, the ruining of gristle becomes evident. In the test group, which took yeast RNA, no signs of arthritis were witnessed for 20 days. Arthritis symptoms, similar to the ones witnessed in the control group on the 14$^{th}$ day, appeared only on the 30$^{th}$ day.

During the development of adjuvant arthritis, back legs became larger in the control animals. In particular, on the 30$^{th}$ day in the control group, the size of back legs evidently increased by 1.04 millimeter (4.9±0.13 in comparison with 3.86±0.1 at the beginning of experiment). In the test group, legs grew only by 0.24 millimeter (4.1±0.11 on the 30$^{th}$ day of experiment from 3.96±0.08 at the beginning of experiment). Hence, yeast RNA delays the development of adjuvant arthritis, which is also supported by a decreased growth rate of back legs.

EXAMPLE 6.2
Action of Yeast RNA on the Activity of NOS in Rat Blood in an Auto-Immune Pathology (Adjuvant Arthritis)

The activity of NOS was evaluated in the blood of normal rats and, on the 3$^{rd}$(I), 8$^{th}$(II), and 14$^{th}$(III) day in the course of an auto-immune pathology in the control group of rats (i.e., not taking yeast RNA) and in the test animals, which were injected with yeast RNA. The results are shown in Table 15 below.

TABLE 15

Action of Yeast RNA Compound on the Activity of NOS in Rat Blood in the Dynamics of Adjuvant Arthritis (in picomol per 1 min per 1 mg of protein; M ± m; n = 5)

|   | Norm | Control | | | + Yeast RNA | | |
|---|---|---|---|---|---|---|---|
|   |   | I $3^{rd}$ | II $8^{rd}$ | III $14^{rd}$ | I $3^{rd}$ | II $8^{rd}$ | III $14^{rd}$ |
| M ± | 30.650 | 236.760 | 24.340 | 111.540 | 70.000 | 40.660 | 33.960 |
| m | 7.352 | 76.418 | 8.596 | 15.777 | 9.245 | 5.052 | 6.036 |
| P1 |  | <0.05 | >0.5 | <0.01 | <0.02 | <0.5 | >0.5 |
| P2 |  |  |  |  | <0.02 | <0.1 | <0.01 |

P1—certainty of difference with respect to the norm (in adjuvant arthritis)
P2—certainty of difference with respect to the control (without yeast RNA)

As shown in Table 15, the control group of animals showed a substantial increase of NOS activity on the $3^{rd}$ and $14^{th}$ day of auto-immune pathology in comparison with norm (30.65±7.35 picomol per 1 min per 1 mg of protein in norm, 236.76±76.42 picomol per 1 min per 1 mg of protein on the $3^{rd}$ day, and 111.54±15.78 picomol per 1 min per 1 mg of protein on the $14^{th}$ day). Such a significant increase in the activity of NOS indicates that activity of the inducible NOS-isoform (iNOS), whose synthesis is initiated by anti-inflammatory cytokines INF-γ, IL-1β, TNF-α, et. al., is the main compound in the calculated activity of NOS.

In the period between the $3^{rd}$ (initiation of the auto-immune process) and $14^{th}$ day (development of pathology), we observed a normalization in the activity of NOS in blood (24.34±8.60 pmol per 1 min per 1 mg of protein). This may probably be attributed to the activated protective reaction of body, and could be induced by inhibition of the expression of NOS as well as by modulation of the stability of its mRNA, or by inhibiting the process of its translation.

In the group of animals which took yeast RNA, initiation of the auto-immune process (on the $3^{rd}$ day) was accompanied by a much smaller (in comparison with the control group) increase in the activity of NOS in blood (70.00±9.24 pmol per 1 min per 1 mg of protein against 236.76±76.42 pmol per 1 min per 1 mg of protein). Moreover, the activity of NOS decreased progressively over the next period in development of auto-immune process (40.66±5.05 pmol per 1 min per 1 mg of protein on the $8^{th}$ day and 33.96±6.04 pmol per 1 min per 1 mg of protein on the $14^{th}$ day).

Therefore, our tests on changes in the activity of NOS in rat blood in the course of an auto-immune process lead to the conclusion that yeast RNA is effective in decreasing the activity of iNOS in the course of an auto-immune process, both during its initiation and in the chronic stage. This property allows the use of yeast RNA in pathological conditions which are accompanied by iNOS induction: inflammatory processes, diabetes, atherosclerosis, tumour, hepatitis, infections, neuro-degenerate diseases (Parkinson's disease, Alzheimer's disease, multiple sclerosis, encephalitis), and others.

EXAMPLE 6.3

Membrane-Protecting Action of Yeast RNA

The tests were conducted in vivo on the model of a chronic auto-immune process, which was accompanied by generation of a great quantity of free radicals (especially, nitric oxide) during the early stage of initiation. The membrane-protecting action of yeast RNA was studied by evaluating acid resistance of erythrocytes in the course of an auto-immune process. Acid resistance characterizes the wholeness of erythrocytal membranes. It increases in the chronic stage of different pathologies and decreases in the acute stage of development (process of initiation). For example, in the early period of development in inflammations, free-radical processes, which are induced by a generation of free radicals of oxygen and nitrogen, including nitric oxide generated by the inducible isoform of NOS (iNOS), are highly activated.

The level of damage in erythrocytes under the influence of various harmful factors in the course of an auto-immune process was evaluated by kinetic indicators of hemolysis, induced by a pH decrease in the environment. Kinetic indicators of hemolysis were recorded; the number of damaged cells was determined spectrophotometrically in equal periods of time (30 s) by changes in the value of integral light dispersion of erythrocytal suspension ($\lambda$=750 nmol). Absorption spectra were registered by a spectrometer SF-26 (Russia). Acid lysis of erythrocytes was initiated by adding 10 μl of blood, which was diluted 20 times in the isotonic medium 0.14 mol of NaCl+0.01 mol of the citrate-phosphate buffer with pH=2.0–3.5 (volume: 1 ml; density of erythrocytes in suspension: $0.7 \times 10^6$ cells per ml). For such densities, the value of integral light dispersion of erythrocytes depends on the count, size, and shape of cells and is proportional to the number of cells in suspension.

Results are represented in the diagram of acid hemolysis of erythrocytes in Table 16 below, as the integral parameter of this process: total number of acid resistance of erythrocytes was calculated by summing up the products of the number of cells $a_i$ which hemolyzed over the period of time $a_j$ and $t_j$ (total resistance (I)=$\Sigma a_i . et_i$).

Decreased extinction levels on hemolysis diagrams represent the succession of erythrocytes with increased resistances entering hemolysis. Extinction starts decreasing usually 1.5–2 min later after a hemolytic injection (1 ml 0.004N HCl, which was prepared from 0.1N HCl and checked by titration). A lag-period of hemolysis is caused by a pre-hemolysis change in the form of erythrocytes (spherulation). Hemolysis of a single erythrocyte does not exceed 10 seconds. Hence, a 30-second interval between the measurements of existence levels excludes the possibility of counting twice the same erythrocyte undergoing lysis. It follows that, by the photometric registration of hemolysis kinetics, we can calculate, from the derived series of existences with intervals 30 seconds, the percentage of distribution of erythrocytes by resistance groups.

The change of existence from the beginning of hemolysis ($E_b$, $t_b$) to its final completion ($E_e$, $t_e$) is proportional to the number of all cells involved in hemolysis (100%), hence:

$$\Delta E = E_e - E_b = 100\%.$$

This total quantity of erythrocytes which undergo hemolysis (100%) consists of the quantity of erythrocytes which undergo hemolysis each 30 seconds ($E_{i+1} - E_i$) in the interval $t_e - t_b$ = duration of hemolysis:

$$\Delta E = \Sigma E_{i+1} - E_i = 100\%.$$

The results are shown in Table 16 below.

TABLE 16

Action of Yeast RNA Compound on the Acid Resistance
of Erythrocytes in the Dynamics of Adjuvant Arthritis
Total Resistance; M ± m n = 5)

| | | Control | | | + Yeast RNA | | |
|---|---|---|---|---|---|---|---|
| | Norm | I 3$^{rd}$ | II 8$^{rd}$ | III 14$^{rd}$ | I 3$^{rd}$ | II 8$^{rd}$ | III 14$^{rd}$ |
| M + | 712.333 | 95.400 | 448.600 | 1013.800 | 372.600 | 638.800 | 565.800 |
| m | 85.429 | 37.776 | 95.843 | 290.509 | 72.667 | 78.903 | 80.244 |
| P1 | | <0.01 | <0.1 | <0.5 | <0.05 | >0.5 | >0.5 |
| P2 | | | | | <0.02 | <0.2 | <0.2 |

P1—certainty of difference with respect to the norm (in adjuvant arthritis)
P2—certainty of difference with respect to the control (without yeast RNA)

As shown in Table 16, there is total resistance of non-showered rat erythrocytes in the course of an auto-immune process. This indicator is equal to 712±85 for normal eythrocytes. During the initiation of an auto-immune process, total resistance of erythrocytes decreased 7 times and constituted 95±38 units. It was gradually increasing in the course of pathology and reached 1114±290 units on the 14$^{th}$ (III) day.

Such a significant decrease in the acid resistance of erythrocytes indicates substantial changes in plasmatic cellular membranes, which is perhaps due to the oxidation of protein and lipid membrane components by free radicals, including nitric oxide, which are actively generated in this period, and in plasma, from which we can infer a modulation in the contents of free cholesterol, polyamines, and other stabilizers, as well as increased levels of destabilizers, such as polyunsaturated free fatty acids.

Animals which took yeast RNA during the initiation of an autoimmune process did not have such decreased acid resistance of erythrocytes as in the control group. Total resistance was equal to 373±73 units, which, though lower than the norm (P<0,05), is greater than in the control group (P<0,05). During the later periods in development of auto-immune pathology, total resistance of erythrocytes in animals taking yeast RNA was at the normal level.

Therefore, yeast RNA has immune-stabilizing action. Taking into account the main mechanisms of damage in this pathology, which are oxide stress and damage of plasmatic membrane components by free-radicals, we can also conclude that yeast RNA is anti-radical.

What is claimed is:

1. A method of stabilizing acid-challenged erythrocyte membranes of a mammal in need of prevention or treatment of inflammation or an inflammatory-related disorder, which comprises administering to said mammal a composition comprising total yeast ribonucleic acid and a pharmaceutically acceptable vehicle, carrier, or diluent, said composition containing said total yeast ribonucleic acid in an amount effective to stabilize said acid-challenged erythrocyte membranes, wherein said composition is administered so that said ribonucleic acid is present into the mammal's blood.

2. The method in accordance with claim 1, wherein said ribonucleic acid has a nitrogen content of more than 14.5% by weight.

3. The method in accordance with claim 1, wherein said ribonucleic acid has a phosphorus content of more than 8.5% by weight.

4. The method in accordance with claim 1, wherein said ribonucleic acid is administered by an intradermal, hypodermal, oral, intra-abdominal, intramuscular, or intravenous route, or is directly administered to a situs of the inflammation or inflammatory-related disorder.

5. The method in accordance with claim 1, wherein said composition is administered by interabdominal injection.

6. The method in accordance with claim 1, wherein the inflammation or inflammatory-related disorder is inflammatory swelling.

7. The method in accordance with claim 6, wherein the inflammatory swelling is carageenan-induced.

8. The method in accordance with claim 1, wherein the inflammation or inflammatory-related disorder is auto-immune inflammation.

9. The method in accordance with claim 8, wherein the auto-immune inflammation is adjuvant arthritis.

10. The method in accordance with claim 1 wherein the mammal is a rat or a mouse.

11. The method in accordance with claim 1, wherein said composition is administered so that ribonucleic acid is present into the mammal's blood prior to occurrence of the inflammation or inflammatory-related disorder.

12. The method of claim 1 wherein said ribonucleic acid comprises at least about 14.7% by weight of nitrogen and at least about 8.6% by weight of phosphorus.

13. The method of claim 1, wherein said ribonucleic acid comprises at least about 15.16% by weight of nitrogen and at least about 8.6% by weight of phosphorus.

14. The method of claim 1, wherein said ribonucleic acid comprises at least about 15.49% by weight of nitrogen and at least about 9.05% by weight of phosphorus.

15. The method of claim 1, wherein said ribonucleic acid comprises more than 15.0% by weight of nitrogen and more than 9.0% by weight of phosphorus.

16. A method of inhibiting oxidation into arachidonic acid of components of cell membranes of a mammal in need of prevention or treatment of inflammation or an inflammatory-related disorder, which comprises administering to said mammal a composition comprising total yeast ribonucleic acid and a pharmaceutically acceptable vehicle, carrier, or diluent, said composition containing said total yeast ribonucleic acid in an amount effective to inhibit oxidation into arachidonic acid of components of cell membranes of the mammal, wherein said composition is administered so that said ribonucleic acid is present into the mammal's blood.

17. The method in accordance with claim 16, wherein the mammal is a rat or a mouse.

18. The method in accordance with claim 16, wherein said composition is administered so that ribonucleic acid is present into the mammal's blood prior to occurrence of the oxidation into arachidonic acid of components of cell membranes.

19. A method of reducing an amplitude of variations of NO-synthetase activity induced by inflammation or inflammatory-related disorder in a mammal, which comprises administering to said mammal a composition comprising total yeast ribonucleic acid and a pharmaceutically acceptable vehicle, carrier, or diluent, said composition containing said total yeast ribonucleic acid in an amount effective to reduce the amplitude of the variations of NO-synthetase activity in the mammal, wherein said composition is administered so that said ribonucleic acid is present into the mammal's blood.

20. The method in accordance with claim 19 wherein the mammal is a rat or a mouse.

21. The method in accordance with claim 19 wherein said composition is administered so that ribonucleic acid is present into the mammal's blood prior to occurrence of increased NO-synthetase activity.

22. A method of inhibiting thrombocyte aggregation induced by inflammation or inflammatory-related disorder, which comprises administering to a mammal in need of such treatment a composition comprising total yeast ribonucleic acid and a pharmaceutically acceptable vehicle, carrier, or diluent, said composition containing said total yeast ribonucleic acid in an amount effective to inhibit thrombocyte aggregation, wherein said composition is administered so that said ribonucleic acid is present into the mammal's blood.

23. The method in accordance with claim 22, wherein the mammal is a rat or a mouse.

24. The method in accordance with claim 22, wherein said composition is administered so that ribonucleic acid is present into the mammal's blood prior to the inflammation or inflammatory-related disorder.

* * * * *